(12) United States Patent
Lefere et al.

(10) Patent No.: US 7,684,852 B2
(45) Date of Patent: Mar. 23, 2010

(54) SYSTEM, FORMULATION, KIT AND METHOD FOR TAGGING COLONIC RESIDUE IN AN INDIVIDUAL

(75) Inventors: Philippe Lefere, Hooglede (BE); Archie Williams, Smithtown, NY (US)

(73) Assignee: Bracco Diagnostics Inc., Princeton, NJ (US)

( * ) Notice: Subject to any disclaimer, the term of this patent is extended or adjusted under 35 U.S.C. 154(b) by 707 days.

(21) Appl. No.: 10/510,368

(22) PCT Filed: Apr. 5, 2003

(86) PCT No.: PCT/US03/10558

§ 371 (c)(1),
(2), (4) Date: Oct. 19, 2004

(87) PCT Pub. No.: WO03/086172

PCT Pub. Date: Oct. 23, 2003

(65) Prior Publication Data

US 2005/0175542 A1    Aug. 11, 2005

Related U.S. Application Data

(60) Provisional application No. 60/370,661, filed on Apr. 6, 2002.

(51) Int. Cl.
*A61B 6/00* (2006.01)
*A61B 5/05* (2006.01)
*A61K 49/00* (2006.01)
*A61K 49/04* (2006.01)

(52) U.S. Cl. .................. 600/431; 600/407; 424/9.1; 424/9.4

(58) Field of Classification Search ............... 424/9.1, 424/9.4, 9.41; 128/921; 600/407, 431; 382/128
See application file for complete search history.

(56) References Cited

U.S. PATENT DOCUMENTS 5,260,049 A * 11/1993 Illig et al. .................. 424/9.45

(Continued)

FOREIGN PATENT DOCUMENTS

JP    08-169849    7/1996

OTHER PUBLICATIONS

Cittadini, G. et al., "Bowel Preparation for the Double-contrast Barium Enema: How to Maintain Coating with Cleansing?", 1999, Clinical Radiology, vol. 54, pp. 216-220.*

(Continued)

*Primary Examiner*—Eric F Winakur
*Assistant Examiner*—Katherine L Fernandez
(74) *Attorney, Agent, or Firm*—Alston & Bird LLP

(57) ABSTRACT

This invention relates to a colonic residue tagging system, formulation, kit and method for use in preparing an individual for a predetermined activity which requires tagging at least some colonic residue in a digestive tract such that a medically and/or diagnostically useful procedure can be performed on the digestive tract. Such predetermined activity includes, but is not limited to, colon screenings. In one alternative embodiment, a dietary regimen comprising low residue foods is coordinated with the colonic residue tagging regimen, prior to a predetermined activity, thereby resulting in tagged stool such that a medically or diagnostically useful procedure can be performed on the digestive tract. The present invention also provides an individual sufficient amounts of fluids and nutrition while minimizing the amount of stool formation prior to the predetermined activity. In another alternative embodiment, the foods comprise an effective amount of tagging agent, such that when the food is consumed over time, at least some of the colonic residue in the digestive tract will be sufficiently tagged so that a medically or diagnostically useful procedure can be performed on the digestive tract.

8 Claims, 13 Drawing Sheets

U.S. PATENT DOCUMENTS

| | | | | |
|---|---|---|---|---|
| 5,352,434 | A | * | 10/1994 | Illig et al. ............... 424/9.411 |
| 5,782,762 | A | * | 7/1998 | Vining ....................... 600/407 |
| 6,039,975 | A | * | 3/2000 | Shah et al. ................. 424/473 |
| 6,083,162 | A | | 7/2000 | Vining |
| 6,272,366 | B1 | | 8/2001 | Vining |
| 6,331,116 | B1 | * | 12/2001 | Kaufman et al. ............ 434/262 |
| 6,477,401 | B1 | * | 11/2002 | Johnson et al. ............ 600/431 |
| 6,866,873 | B2 | * | 3/2005 | Stern ......................... 424/725 |
| 2004/0228799 | A1 | * | 11/2004 | Armstrong ................ 424/9.41 |

FOREIGN PATENT DOCUMENTS

| | | |
|---|---|---|
| JP | 2001-048810 | 2/2001 |
| WO | WO 95/22995 | 8/1995 |
| WO | WO 96/13207 | 5/1996 |
| WO | WO 98/32371 | 7/1998 |
| WO | WO 03/086172 A3 | 10/2003 |

OTHER PUBLICATIONS

The Children's Hospital at Westmead, "Fact Sheet: Low Residue Diet", Online, Retrieved on Apr. 5, 2007, Internet: http://web.archive.org/web/20010713061634/http://www.chw.edu.au/parents/factsheets/folowres.htm.*

Callstrom et al., "CT Colonography without Cathartic Preparation: Feasibility Study", Jun. 2001, Radiology, vol. 219, No. 3, pp. 693-698.*

Lauenstein et al., "MR Colonography without Colonic Cleansing: A New Strategy to Improve Patient Acceptance", Oct. 2001, AJR, vol. 177, pp. 823-827.*

Lauenstein et al., "MR Colonography with Barium-based Fecal Tagging: Initial Clnical Experience", Published online before print Feb. 21, 2002, pp. 248-254.*

Bircher et al., "Controlled Clinical Trial of Barium Sulfate Suspensions for Upper Gastrointestinal X-Ray Examinations", Europ. J. clin. Pharmacol., 4, 1971, pp. 38-45.*

American Hospital Formulary Service Drug Information 1994 p. 1580.*

Virtual Colonoscopy, Second International Symposium, Oct. 16-17, 2000, pp. 66-69.

Scientific Program, The Radiological Society of North America 87th Scientific Assembly and Annual Meeting, From Science to Patient Care RSNA 2001, Nov. 25-30, 2001, pp. 578 and 579.

Virtual Colonoscopy, Fourth International Symposium, Oct. 13-15, 2003, pp. 32-37 and pp. 65-67.

Virtual Colonoscopy, First International Symposium, Oct. 1-2, 1998, pp. 19-21, and 94.

Perry J. Pickhardt, et al., Electronic Cleansing and Stool Taggin in CT Colonography: Advantages and Pitfalls with Primary Three-Dimensional Evaluation, AJR:181, Sep. 2003, pp. 799-805.

http://www.viarronix.net/med_com_RSNA01elclean2.asp, Feb. 9, 2005, 2 pgs.

http://www.viarronix.net/med_com_SPIE2002sarang.asp, Feb. 9, 2005, 2 pgs.

http://spiedl.aip.org/getabs/servlet/GetabsServlet?. . ., Feb. 9, 2005, 2 pgs.

Jerome Z. Liang, Virtual Colonoscopy: An Alternative Approach to Examination of the Entire Colon, 10 pgs., Stony Brook, NY.

http://shows.rsna.org/V25/conference/session.cvn?eID=3206999, Dec. 3, 2001, 2 pgs.

http://shows.rsna.org/rsna2002/V40/conference/session.cvn?eID=3108596, Oct. 31, 2002, 1 pg.

Lihong Li, et al., An image segmentation approach to extract colon lumen through colonic material tagging and hidden Markov random field model for virtual colonoscopy, 6 pgs., Stony Brook, NY.

RSNA 2002, Scientific Program, 88th Scientific Assembly and Annual Meeting, Supplement to Radiology, Nov. 2002, vol. 225(P), pgs. 584-585 and 979.

Material Provided by Third Party in the form of a patent application. We are unsure whether it has been filed or published, but due to an abundance of caution, we are providing it to the Examiner.

Chen et al., "Electronic Colon Cleansing by Colonic Material Tagging and Image Segmentation for Polyp Detection: Detection Model and Method Evalation," *Nuclear Science Symposium Conference Record, 2000 IEEE* (Meeting Date: Oct. 15, 2000-Oct. 20, 2000), 2000, pp. 18/131-18/135, vol. 3, Lyon, France, http://ieeexplore.ieee.org/xpl/freeabs_all.jsp?tp=&arnumber=949253&isnumber=20545.

Callstrom et al., "CT Colonography Without Cathartic Preparation: Feasiblity Study," *Radiology*, 2001, pp. 693-698, vol. 219, No. 3.

Chen et al., "A Novel Approach to Extract Colon Lumen from CT Images for Virtual Colonoscopy," *IEE Transactions on Medical Imaging*, 2000, pp. 1220-1226, vol. 19, No. 12.

Japanese Pharmaceutical Excipients Directory, Yakuji Nippo Limited., Jan. 14, 1994, 1st Edition, p. 77, pp. 130-131.

* cited by examiner

Example of tagged fluid.

Tagged fluid moulding the colonic semicircular folds

40 % 25-12.5-12.5 ml
= TagitolV + cleansing

Example of tagged stool.

Same as previous

Examples of smaller and larger stool balls labeled with barium.

Example of tagged stool and small tagged fluid levels.

Same as previous

Large homogeneously tagged fluid levels in the transverse and descending colon.

Example of tagged fluid.

Tagitol (2.1 %) + cleansing

Non-tagged "material" Surrounded by a small Barium film. Image highly Suspicious of polypoid lesion, confirmed by conventional colonoscopy.

Example of polypoid lesion surrounded by tagged residue.

Tagitol V + cleansing

Patient prepared without cathartic cleansing, with Nutra Prep, the hydration control and barium as the sole tagging agent.

A tiny barium film covers the colonic surface.
An eventual polypoid lesion would easily be recognized as a non-tagged lesion.
High densities are obtained.

Patient prepared without cathartic cleansing, with Nutra Prep,
the hydration control and barium as the sole tagging agent.

Tagitol 2.1- no cath cleans - 1 day

Results of the electronic labeling.
All stool with densities ≥ 150 H.U. was electronically labeled.

SYSTEM, FORMULATION, KIT AND METHOD FOR TAGGING COLONIC RESIDUE IN AN INDIVIDUAL

CROSS REFERENCE TO OTHER APPLICATIONS

This application claims priority from U.S. Provisional Application Ser. No. 60/370,661, filed Apr. 6, 2002, which is incorporated herein by reference in its entirety.

I. FIELD OF THE INVENTION

This invention relates to a system, formulation, kit and method for use in tagging colonic residue, such as stool, in an individual prior to a predetermined activity, including but not limited to a medical or diagnostic procedure. In one alternative embodiment, the present invention provides an individual one or more doses of a tagging agent, together with sufficient fluids and nutrition to enable the individual to conduct daily, routine activities while minimizing the amount of stool formation prior to the predetermined activity.

II. BACKGROUND OF THE INVENTION

As used herein the term "digestive trace" includes, but is not limited to, the mouth, pharynx, esophagus, stomach, small intestine and large intestine. Also, as used herein, the terms "colonic residue" and "residue" include any composition of matter resulting from digested food and other body waste which has not been absorbed by the body's digestive system. Such residue includes, but is not limited to, any solid, semi-solid or liquid stool matter.

Removal of stool matter from the digestive tract has historically been necessary to effectively screen for gastrointestinal abnormalities, including, but not limited to, cancer such as colon cancer. Since colon cancer is a highly treatable and often curable if detected early, screening tests for detecting premalignant polyps and colorectal cancers at stages early enough for complete removal are very important.

Colon screening procedures include, for example, barium enema, sigmoidoscopy and fiberoptic colonoscopy. The most recent technological advancement in colon screening is virtual colonoscopy/CT Colonography. This procedure utilizes computer reformation of radiologic images to form images of the colon in two or three dimensions. Historically, sufficient amounts of stool matter had to be removed from the colon prior to a virtual colonoscopy procedure. This is because stool and colon lesions are not easily distinguishable in computer tomography or other radiologic modality images, thus preventing physician's ability to distinguish pathology from retained fecal debris. In one alternative embodiment, the present invention is a method for marking colonic residue (e.g., stool) present in an individual's digestive tract (e.g., colon) with a radiopaque material before the digestive tract is imaged. The marked stool, for example, can then be readily identified in the images. Alternatively, the marked stool can be identified and/or electronically removed from the images.

U.S. Pat. No. 6,477,401 to Johnson et. al. is directed to a method of generating colonography images of a patient's unprepared colon for colorectal screening. This method requires providing the patient at least 10 grams of stool marker in doses over at least a 48 hour administration period.

The present invention is distinguishable, and is more advantageous over the methods disclosed in the '401 patent. For example, in one alternative embodiment of the present invention, the individual's stool is sufficiently marked within 24 hours. This improves the patient's compliance to the tagging and/or dietary regimen prior to the predetermined activity. Also, in contrast to the '401 patent, in one alternative embodiment, the present invention limits the amount of tagging doses to 3 or less over a 24-hour administration period. This is accomplished by providing small volumes of liquid containing high concentrations of tagging agent. Further, the present invention minimizes the amount of stool retained in the gastrointestinal tract (e.g., colon) by administering a low residue diet to the individual prior to the predetermined activity. This provides several advantages. For example, in some situations, the physician may require the individual to undergo a laxative prior to the predetermined procedure. Because the present invention minimizes the production of stool, the patient need only take a mild laxative, as opposed to a cathartic. Also, because low amounts of stool are present, there is no need to utilize special software to remove the marked stool from the images of the individual's tissue, for example. All considered, the present invention, in contrast to the '401 patent, provides a cleaner gastrointestinal tract (e.g., colon) with less fluid and less retained stool. Other advantages of the present invention are described herein.

There is, therefore, a need for a colonic residue tagging regimen which effectively marks colonic residue in the digestive tract while providing the user with a sufficient level of calories and nutrition to conduct routine, daily activities. Additionally, there is a need for a tagging regimen which is readily useable and convenient, which also minimizes the amount of fluid or stool formation prior to the predetermined activity. In addition, there is a need for a dietary regimen to be used in conjunction with a tagging regimen, while at the same time facilitating user compliance since current tagging regimens are difficult or painful to complete. The consequences of non-compliance can be great. For example, noncompliance can result in an ineffective colon screening.

III. SUMMARY OF THE INVENTION

It is an object of the present invention to provide an easy and effective colonic residue tagging system, formulation, kit and method for use in preparing an individual prior to a predetermined activity which requires tagging at least some colonic residue.

It is also an object of the present invention to provide a low residue dietary system, formulation, kit and method to be used with a tagging regimen for preparing individuals for a predetermined medical diagnostic procedure including, but not limited to, colon screening.

Further, it is an object of the present invention to provide a variety of individually prepackaged, ready to eat or easy to prepare solid or liquid foods which can be consumed as part of a regimen for tagging at least some colonic residue in the digestive tract prior to a predetermined activity.

It is also an object of the present invention to provide a variety of foods containing an effective amount of tagging agent, such that when the food is consumed, at least some of the colonic residue in a digestive tract will be sufficiently tagged so that a medically and/or diagnostically useful procedure can be performed on the digestive tract.

It is another object of the present invention to provide a low residue dietary regimen comprising sufficient calories and nutrition such that routine, daily activities may be performed and no nutritional detriment is suffered by the user while undergoing the dietary regimen in conjunction with a colonic residue tagging regimen in preparation of a predetermined activity.

Other objects, features, and advantages of the present invention will be apparent to those of ordinary skill in the art in view of the following detailed description of the invention and drawings.

IV. BRIEF DESCRIPTION OF THE DRAWINGS

V. DETAILED DESCRIPTION OF THE INVENTION

Figure 1:
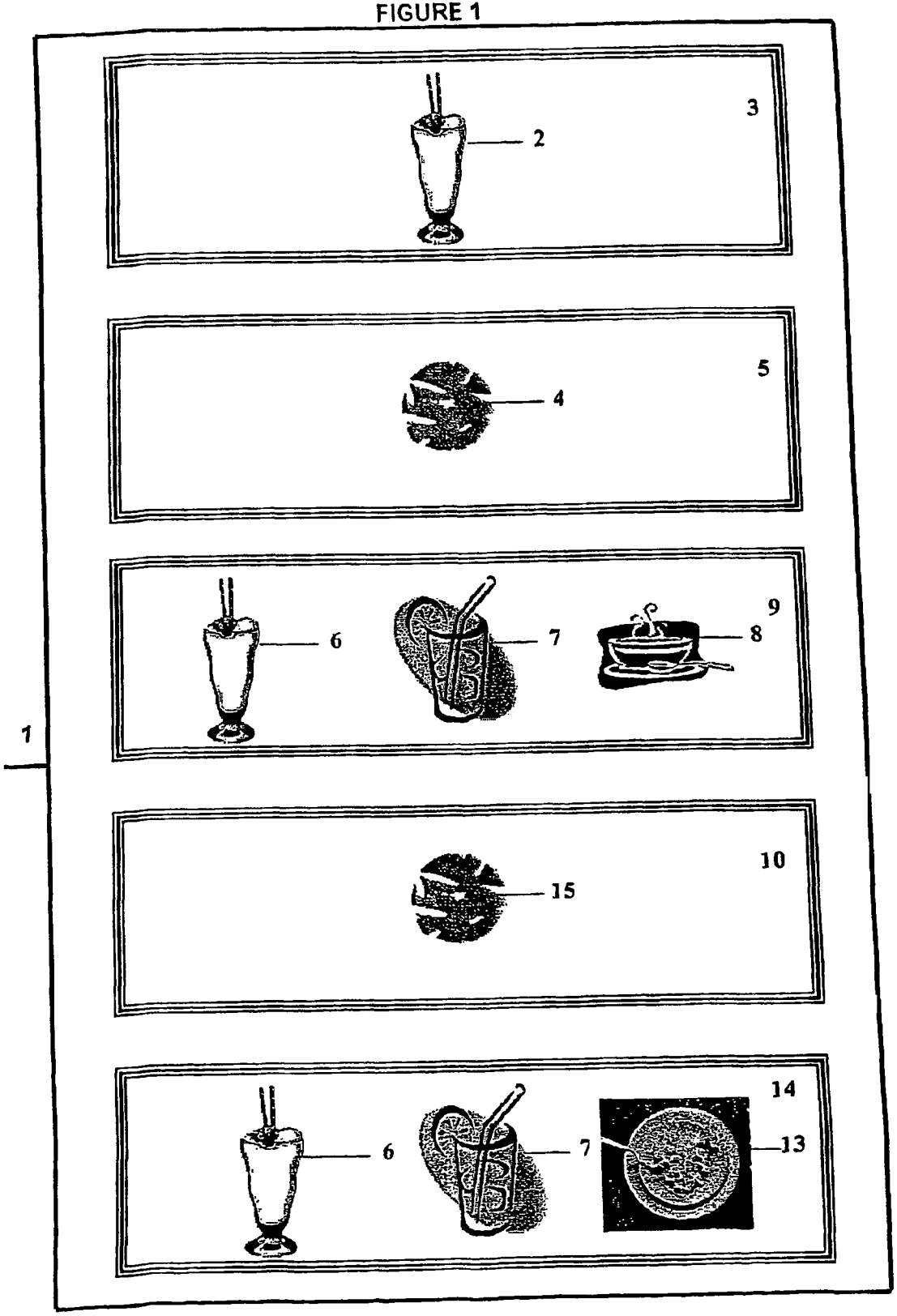
FIG. 1 is a non-limiting example of a container comprising the food items of the present invention.

The present invention provides a colonic residue tagging system, kit, formulation and method for use in preparing an individual for a predetermined activity, including but not limited to, an activity which requires tagging at least some colonic residue in a digestive tract. As used herein, the phrase "tagged digestive tract" or phrases similar thereto, include but are not limited to a digestive tract that has at least some colonic residue marked with a tagging agent such that at least some of the residue can be differentiated from surrounding tissues.

A predetermined activity includes, but is not limited to, any activity imaging a tagged digestive tract. In one embodiment, the predetermined activity may include, but is not limited to, a medical diagnostic procedure, which includes, but is not limited to, gastrointestinal screening (e.g., colon screening) such as virtual endoscopy, which includes, but is not limited to, CT colonography and MR colonography. Other diagnostic procedures may include ultrasound, flat panel imaging methodologies, sigmoidoscopy, endoscopy or fiberoptic colonoscopy. Other methodologies may be performed in a conventional manner such as, for example, those described in U.S. Pat. No. 5,891,030; U.S. Pat. No. 5,782,762 and U.S. Pat. No. 5,920,319. The images generated from the above procedures may be three dimensional (3D) images. Commercially available software programs such as Voxel/View from Vital Images may be used for this purpose. Alternatively, the screening diagnoses can be obtained through the use of two dimensional (2D) colonography images processed in accordance with the methodologies identified herein. In one alternative embodiment, the present invention is a method of marking colonic residue with identifiable material before one or more sections of the digestive tract is imaged.

The present invention also provides for a combined low residue dietary and colonic residue tagging system, kit, formulation and method for use in preparing an individual for a predetermined activity. The dietary regimen of the present invention comprises one or more food items. These items include any liquid, solid or semi-solid food providing, in whole or in part, the requisite amounts of nutrition described herein. Such food items may include, but are not limited to, soup products, protein supplements, grain foods, starch foods, fruit or vegetable foods, nutritional drinks or beverages.

International Appl. No. PCT/US01/32039 and U.S. application Ser. No. 10/177,276 relate to a nutritional dietary system, formulation, kit and method for use in preparing an individual for a predetermined activity. Both of these applications are incorporated herein by reference. Such application discloses several nutritional dietary regimens. Each of these dietary regimens are suitable for use in the present invention, provided the requisite amount of tagging agent is incorporated into the dietary regimen, as discussed herein.

In use, the colonic tagging agents of the present invention are preferably consumed over about a 20- to 36-hour period, or a 20- to 48-hour period, or a 20- to 36-hour period, or a 24- to 28-hour period, more preferably over about a 24-hour period prior to a predetermined activity. In addition, the food items of the present invention, together with suitable tagging agents, may be consumed over a 72-hour period, a 48-hour period, a 24- to 36-hour period, a 36- to 48-hour period and 48- to 72-hour period prior to a predetermined activity.

A. Tagging Regimens

The tagging agents of the present invention may include any composition that can label and/or mark colonic residue so that such residue can be differentiated from surrounding tissue during a predetermined activity. Suitable tagging agents, include but are not limited to, barium-based compounds, such as barium sulfate, for example. Other agents may include iodine-based compounds, such as non-ionic or ionic iodine or any combination of the above mentioned compounds.

In the present invention, doses of tagging agent may be administered in a liquid, semi-liquid, powder or solid form. For example, the tagging agent may be consumed as a drink. Also, the tagging agent may be consumed as a suspension or swallowed as a tablet, capsule or caplet. In another alternative embodiment, the total amount of tagging agent administered to the individual prior to the predetermined activity may be at least 1 g, 5 g, 10 g, 50 g, 70 g, 10 g, 150 g, 200 g, 300 g, 350 g, 400 g, 450 g, 500 g, 550 g, 600 g or more. The preferred amount ranges from about 15 g to 30 g, more preferably about 20 g to about 30 g.

In addition, the tagging agent can be incorporated into any of the food items in the present nutritional dietary system described herein. For example, the tagging agent may be added to a pudding, yogurt-like food product, soup nutritional drink or other food item with or without nutritional value. Methods for including the tagging agent into the food item(s) may include adding the agent while the food is being prepared or cooked, or it may be added afterwards. For example, the tagging agent may be added directly to pre-made yogurt-like food products, pudding, nutritional drinks or soups, for example. The amount of tagging agent in the one or more food items may range from about 0.01 g to about 200 grams; 0.01 g to about 150 g; 0.01 g to about 100 g; 0.01 g to about 50 g; 0.01 g to about 25 g; 0.01 g to about 5 g; 0.01 g to about 1 g; 0.01 g to about 700 mg. In all, the total amount of tagging agent consumed by the individual prior to the predetermined activity may be at least 1 g, 5 g, 10 g, 50 g, 70 g, 100 g, 150 g, 200 g, 250 g, 300 g, 350 g, 400 g, 450 g, 500 g, 550 g, 600 g or more. In another alternative embodiment, the food item (containing tagging agent) may be consumed over a 20- to 48-hour period, or a 36- to 48-hour period; or a 48- to 72-hour period or a 24- to 28-hour period. Such food item may also be administered over a 3- to 5-day period.

In the present invention, the tagging agent may be provided in a suspension. Such suspension may comprise water, a sugar-based compound, viscosity agents, such as citric acid and suspending agents or gums. In one alternative embodiment, the commercially available product Tagitol® may be used in the present invention. Tagitol® is sold by E-Z-EM, Westbury, N.Y. Tagitol® is a low-density suspension of barium sulfate. It is lemon-lime-flavored and provided in 250 ml dose bottles.

In the present invention, an individual may receive 1 to 10 doses of tagging agent over a period of 1-5 days. Each individual dose may range from 0.1 to 100% w/v tagging agent. In one alternative embodiment, the dosing regimen for the tagging agent is administered over a 20-to-36-hour period, preferably a 24-hour period, may be as follows:

| Dose | | % W/V Tagging Agent |
|---|---|---|
| 1 | 50 ml | 40% |
| 2 | 250 ml | 2.1% |
| 3 | 250 ml | 2.1% |
| 4 | 250 ml | 2.1% |
| 1 | 250 ml | 2.1% |
| 2 | 250 ml | 2.1% |
| 3 | 250 ml | 2.1% |
| 1 | 20 ml | 40% |
| 2 | 20 ml | 40% |
| 3 | 20 ml | 40% |

In another alternative embodiment, an individual may receive 1, 2, 3, 4, 5, 6, 7, 8, or 9 doses of tagging agent over a period of about 48 hours, or 36 hours, preferably 20- to 24-hours, most preferably 24 hours. Preferably, the individual receives less than 7, 6, 5, 4, 3 or 2 doses over a 48-hour, or 36-hour, preferably 20 to 24 hours, most preferably a 24-hour period. In another alternative embodiment, the individual may receive only 1 or 2 doses over a 16, 15, 14, 13, 12, 11, 10, 9, 8, 7, 6, 5, 4, 3, 2 or 1 hour period prior to the predetermined activity.

The volume of each individual dose may range from about 10 ml to about 500 ml; about 10 ml to about 400 ml; about 10 ml to about 300 ml; about 10 ml to about 250 ml; about 10 ml to about 200 ml; about 10 ml to about 100 ml; about 10 ml to about 50 ml. In one alternative embodiment, the volume of each individual dose may range from about 20 ml to about 60 ml; about 20 ml to about 50 ml; about 20 ml to about 40 ml; or about 20 ml to about 30 ml.

Each individual dose may range from about 2% to 100%; about 2% to 90%; about 2% to 80%; about 2% to 70%; about 2% to 60%; about 2% to 50%; about 2% to 45%; about 2% to 40%; about 2% to 35%; about 2% to 30%; or about 2% to 25% w/v tagging agent. The dose may also range from about 10% to 80%; 15% to 75%; 20% to 70%; 25% to 55%; 30% to 60%; 35% to 55%; or 40% to 50% w/v tagging agent. Further, the dose may range from about 1.5% to 60%, 1.5% to 50%; 1.5% to 40%; 1.5% to 30%; 1.5% to 20%; 1.5% to 10%.

In another alternative embodiment, an individual may receive less than 7 doses. Each individual dose comprising greater than 2% w/v tagging agent. Also, the doses may be administered over about a 24-hour period.

Each of the above-described doses may take the form of a liquid suspension and/or be administered by suspending the tagging agent in a liquid whereby the individual drinks the liquid. The process of the present invention may be practiced without administering the tagging agent in pill form. Also, the tagging agent may be incorporated into a food item, as described herein.

In one alternative embodiment, the final dose of tagging agent is administered to the individual at least 12 hours prior to the predetermined activity. In another alternative embodiment, the final dose of tagging agent may be administered about 16, 15, 14, 13, 12, 11, 10, 9, 8, or 7 hours prior to the predetermined. This dosing regimen enables the individual to sleep through the night without waking up to consume one or more doses of tagging agent the night before the predetermined activity. For example, the final dose of the tagging agent may be administered with the individual's dinner the night before the predetermined activity.

In one alternative embodiment, the tagging agents may be combined with a sugar-based compound. Such compounds may include any simple sugar compounds, or any, other transient compound or agent capable of causing the small bowel to hyperscret fluid. This in effect partially fills the small bowel with fluid increasing the total volume of contents in the small bowel, thus causing an increase in the peristaltic activity resulting in rapid transport of the tagging agent into the colon. When the tagging agent arrives in the colon it is sufficiently mixed with the colonic residue and body fluids. The transport of this volume causes the colon to evacuate it's contents to make room for the contents coming down through the system. The low residue and fiber structure of the nutritional system leaves at least some of the residue tagged.

The sugar-based compounds for use in the present invention may include, but are not limited to, manosaccharides and polysaccharides such as D-mannose, D-galactose, nanionic seed polysaccharide, straight chain mann grouping with branching on every mannose by one gluctose unit, Beta-D-man, alpha-D-gal, D-glcA, D-galA, L-gul, beta-D-man, alpha-D-gal (4:1), D-glucuronic aced, D-galacturones aud, L-glucuronic acid, sorbitol, manotol. The preferred sugar-based compounds are Sorbitol or Mannitol.

The preferred amount of Sorbitol and or Mannitol to be combined with the tagging agent is about 0.1% to about 3% or about 1.5 to about 2.5% by volume, or up to any amount below the USP manograph standard for laxative concentration levels for these compounds. For example, a preferred tagging regimen may include administering a suspension comprising 40% Barium Sulfate and 1.5% or 2.5% Sorbitol to an individual.

The low residue and low fiber design of the nutritional diet yields minimal residue in the colon, thus reducing the requirement to thoroughly clean the colon before a medical diagnostic procedure, for example. Remaining residue in the colon is tagged for easy differentiation from surrounding tissue.

In one alternative embodiment, by undergoing the dietary regimen of the present invention, a predetermined volume of fluid is delivered to the GI tract. Additionally, the individual takes the tagging agent and all of these components contribute to the controlled fluid intake of the individual. While the nutritional components satiate the individual they introduce sufficient volume of fluid in combination with the tagging agent and the increased peristaltic effect of the sorbital or sorbital like components in the tagging agent. By controlling the volume of fluid, the body evacuates the contents of the colon to make room for the contents that are transiting through the small bowel.

U.S. Pat. No. 5,782,762 describes preparing a patient's colon by feeding the patient a low residue diet combined with a contrast agent (such as low density barium, for example, 1.5% w/v barium) for about 3 days. According to the patent, this procedure serves to homogeneously opacity any retained stool so that the image of the feces can be subtracted from the final display using image processing techniques. By contrast, in one alternative embodiment of the present invention, the tagging agent impregnates the stool non-homogeneously. That is, the tagging agent is distributed non-uniformly based on the stool's structure. Stool density varies within a certain volume of stool. It can range from dense to thin based on the material or waste in the stool.

B. Hydration

In using the present invention, it is necessary that the individual maintain sufficient hydration. Such hydration being sufficient to maintain the individuals normal physiological properties, and to control the amount of fluid retained in the digestive tract.

Thus, the dietary and tagging regimen of the present invention may be used with a hydration regimen. Suitable hydration regimens include, but are not limited to, regimens requiring at least some fluid intake, including, but not limited to, water or fruit drinks. The hydration portion of the present invention is structured to replace the water lost through normal voiding (urination) respiration and perspiration. By limiting the intake of fluids, the patient's normal physiological properties are maintained, and the amount of fluid present in the patient's bowel is reduced. This goal may be complemented by not having to use an aggressive cathartic like PEG or any of the saline cathartics.

Excessive fluid intake can generate fluid levels in the colon that can hide and/or obscure normal and pathologic segments of the colon during a medical diagnostic procedure, such as virtual colonoscopy. Thus, a suitable amount of fluid intake for use in the present invention is one that replaces the fluids used by the body while not creating fluid levels in the colon that can hide and/or obscure normal pathologic segments in the colon which otherwise adversely affect the outcome of predetermined activity.

In one embodiment, based on about a 20- to 24-hour regimen, the food items and doses of tagging agent may collectively provide at least about 1 to 4 liters of fluid, preferably about 1 to 3.5 liters, more preferably about 1 to 3 liters or 1.5 to 2 liters. If the food items and doses of tagging agent do not provide these amounts of fluid, the present invention may be supplemented or the individual may be provided with additional fluids to achieve such amounts during that period of time. It has been discovered that controlling or regulating the individual's fluid intake to the above specified amounts greatly improves the readiness of the individual's gastrointestinal tract (e.g., colon) for the predetermined activity (e.g., colon screening). For example, the greater fluid presence in an area of stool, the lower the concentration of tagging agent, rendering a lower Hounsfield value (HU) for that particular area. The denser the stool, the less fluid present, causing increased concentration of the tagging agent in the stool. The higher the tagging agent concentration, the higher the HU for that particular area of stool. Increasing the HU value allows for easy differentiation between stool and surrounding tissues, recognizing that untagged stool has a similar density to that of the surrounding normal or pathological tissues.

C. Nutrition

1. Calories

The food items of the present invention may collectively provide an individual an appropriate caloric intake level over the time period in which the invention is utilized. In one alternative embodiment, based on about a 20- to about a 36-hour dietary regimen, the food items may collectively provide at least 100 calories, preferably in a range of about 400 to about 3,000 calories, and more preferably in a range of about 600 to about 2,000 calories. In an alternative embodiment, based on about a 20- to 36-hour dietary regimen, the food items may collectively provide more than about 600 calories, more preferably in a range of about 1,000 to about 1,800 calories, and most preferably in a range of about 1,500 to about 1,600 calories. In another alternative embodiment, the food items may collectively provide a range of about 1,000 to about 2,000 calories, from about 1,400 to about 1,600 calories, and from about 1,600 calories. The total calories of the food items of the present invention are preferably sufficient to enable an average sized individual to perform routine daily activities without experiencing the dizziness, fatigue and lightheadedness ordinarily experienced with a clear liquid diet.

2. Dietary Fiber

The food items of the present invention may collectively provide an individual an appropriate amount of dietary fiber over the time period in which the invention is utilized. In one alternative embodiment, based on about a 20- to 36-hour dietary regimen, the food items may collectively provide at least 0.5 g of dietary fiber, preferably in a range of about 0.5 g to about 50 g of dietary fiber, more preferably in a range of about 0.5 g to about 20 g, and even more preferably in a range of about 2 g to about 15 g, and most preferably from about 2 g to about 6 grams. In an alternative embodiment, based on about a 20- to about a 36-hour dietary regimen, the food items may collectively provide less than about 15 g of dietary fiber. Also, in an alternative embodiment, based on about a 20- to about a 36-hour dietary regimen, the food items may collectively provide about 20 g to about 60 g of dietary fiber, or 20 g to 30 g, 30 g to 40 g, 40 g to 50 g, 50 g to 60 g, or 60 g to 100 g. It has been found that a dietary regimen containing low amounts of dietary fiber, when used in conjunction with a tagging regimen, can eliminate the need for consuming high-volume purgative drinks or high sodium cathartic cleansing drinks, which can be difficult to consume for some individuals. Examples of foods that may be consumed by a patient on a low residue, low fiber diet are listed in Table 1 in U.S. Appl. No. 60/370,661. Also, in this application, Table 2 lists an example of a 24-hour low fiber diet that may be used in the present invention.

The food items of the present invention may also collectively provide an appropriate amount of protein, carbohydrates, fats, sodium, potassium, sugars, vitamins or minerals over the time period in which the invention is utilized by an individual. Suitable amounts of these nutrients are set forth at pages 9-16 of U.S. Prov. Appl. No. 60/370,661.

3. Solid-Material

The individual food items of the present invention may individually or collectively provide a suitable amount of solid material, which includes particulate material. In one alternative embodiment, based on about a 20- to about a 36-hour dietary regimen, the present invention may provide up to approximately 1000 grams of solid material, as measured in dry form. In another embodiment, the present invention provides about 10 g to about 1000 grams of solid material, preferably about 100 g to about 800 g, more preferably about 200 g to about 700 g, and most preferably about 400 g to about 600 g. Table 5 shows the approximate total weight of one alternative embodiment of the dietary regimen of the present invention:

TABLE 5

Example of Approximate Dry Weight of Dietary Regimen

| Food Item | Approximate Weight Dry | Approximate Net Weight Prepared |
| --- | --- | --- |
| Stroganoff | 37.62 | 163.11 |
| Chicken Noodle Soup | 36.39 | 160.88 |
| Potato Poppers | 29.36 | 29.36 |
| Applesauce | 70.15 | 113.40 |
| Vanilla Shake (3) | 66.96 (3) | 261.46 (3) |
| Lemon Drink Mix (2) | 6.95 (2) | 216.13 (2) |
| Chocolate Power Bar (2) | 50.69 (2) | 50.69 (2) |
| Total | 489.68 | 1784.77 |
| Total Percentage of Solid Material Included in Diet | 27.4 | — |

In another alternative embodiment of the present invention, based on about a 20- to about a 36-hour dietary regimen, the food items may collectively comprise at least about 1% by weight of solid material, preferably in a range of about 1% to about 70%, more preferably about 10% to about 30%, and most preferably about 20% to about 30%. In another embodiment, the food items of the present invention may collectively provide about 30% to 40%, 40% to 50%, 50% to 60%, 60% to 70%, 70% to 80%, 80% to 90%, and 90% to 100% by weight of solid material. In another embodiment, the food items of the present invention, individually or collectively, provide sufficient solid material to cause natural peristalsis in the digestive tract when consumed.

D. Food Items of the Present Invention

The present invention comprises one or more food items, including, but not limited to soup products, protein supplements, grain foods, starch foods, fruits or vegetables, nutritional drinks, and beverages. Specific food items suitable for the present invention are described in International Appl. No. PCT/US01/32039 and U.S. application Ser. No. 10/177,276, which are incorporated herein by reference. Each food item of the present invention may be individually prepackaged. In addition, one or more of the food items may be nutritionally enhanced by fortification of vitamins and minerals.

A food item suitable for use in the present invention is one that forms no residue in the digestive tract or that forms an amount of food residue which does not impede or otherwise adversely affect a predetermined activity. Individual food items of the present invention may be in the form of solids, semi-solids or liquids and may include, but are not limited to, soup products, protein supplements, grain foods, starch foods, fruit or vegetables foods, nutritional drinks and beverages. In contrast to the prior art, the liquid food items of the present invention may or may not be clear. Each of the food items of the present invention are discussed in more detail below.

The coloring used in the food items of the present invention, particularly in the nutritional drinks and beverages, may be limited by the purpose for which the food residue is being removed from the individual's digestive tract. For instance, a food item containing red coloring may not be suitable for an individual preparing for an optical colonoscopy, as the red coloring may interfere with the test results of such procedure.

As discussed, the tagging agent may be added to a food item. One or more such foods may be included in the meal kit described herein.

E. Synergistic Effect When Utilizing Nutrition/Hydration/Tagging

If no laxative is used to cleanse the colon prior to the predetermined activity, it was believed that the retained stool would impede the screening procedure. Surprisingly, however, it has been discovered that no laxative regimen is required, because the dietary regimen provides manageable amounts of retained stool, and the amount of stool is such that it can be sufficiently tagged with a tagging agent. By combining an appropriate nutrition, hydration and/or tagging regimen, CT or MR Colonography may be performed without a colon cleansing system, thus further increasing patient compliance. If the predetermined activity requires bowel cleansing, then the individual need only be given a mild laxative, as opposed to a cathartic. Additionally, by combining an appropriate nutrition, hydration and/or tagging regimen, the images of the individual's gastrointestinal tract (e.g., colon) may be screened for abnormalities (e.g., cancer) without removing (electronically or otherwise) the marked stool from the images. That is, the images may be screened for the presence of any abnormalities with the marked stool present in the images.

F. Patient Compliance

Other features of the present invention include improved user compliance and quality of life as compared to conventional techniques for preparing an individual for a medical diagnostic procedure, such as a colonoscopy. For example, the present invention requires less doses of tagging agent to be administered, and the volume of each dose is less than those administered in the prior art. Also, the tagging regimen of the present invention may be completed in less than 48 hours, for example. In some instances, the tagging regimen may be completed in 24 hours, or less. Further, the present invention minimizes the amount of stool retained in the gastrointestinal tract (e.g., colon). This provides several advantages. For example, in some situations, the physician may require the individual to undergo bowel cleansing prior to the predetermined procedure. Because the present invention minimizes the production of stool, the individual need only take a mild laxative, as opposed to a cathartic. Non-limiting mild laxatives are described in Appl. Ser. No. PCT/US01/32039, at page 37, for example. Thus, the tagging regimen of the present invention is less time consuming and more comfortable to the individual preparing for a predetermined activity, thereby resulting in improved patient compliance with the preparation process.

In the present invention, the individual may drink a small amounts of tagging agent when undergoing a low residue diet and the hydration regimen of the present invention patents. Adequate tagging may be obtained with a barium volume ranging between 50 and 750 ml. This reduction in barium volume results in all increased patient compliance. A second improvement of patient compliance is related to the fact that there was no difference in tagging effectiveness when patients were taking barium over 1 or 2 days. Reducing the tagging agent intake to 1 day will also increase patient compliance.

While the level of compliance of any of these procedures depends in part on the motivation and drive of the individual, compliance nevertheless may also be influenced by identifiable and controllable factors such as the ease with which the diet or technique may be utilized, as well as the taste, appearance, and in general, the desirability of the items to be eaten.

G. The System and Kit of the Present Invention

The system and/or kit of the present invention represents an improvement over traditional techniques or products used to prepare individuals for medical diagnostic procedures. The present invention is designed to facilitate user compliance by providing a variety of solid, semi-solid and liquid food items for consumption, together with a tagging agent for marking the colonic residue. Additionally, the present invention is designed to improve the user's quality of life by supplying the user with sufficient caloric intake and nutrition such that daily activities may be undertaken. Also, the residue is sufficiently tagged such that it can be distinguished from surrounding tissues during a diagnostic procedure, for example.

In one alternative embodiment, the nutritional dietary system and kit of the present invention comprises one or more food items arranged in one or more separate feedings, for example, three feedings. Examples of suitable embodiments, systems and kits of the present invention, are described in International Appl. No. PCT/US01/32039 and U.S. application Ser. No. 10/177,276, which are incorporated herein by reference.

In one embodiment of the present invention, an individual obtains the present invention comprising one or more individually prepackaged food items and tagging agents. The invention also comprises instructions for coordinating the food items for use together as a single dietary system, as well as instructions for coordinating the tagging agent with the dietary system. The instructions may be positioned on one or more surfaces of the container holding the food items and/or tagging agent, or the instructions may be provided on a separate sheet, or any combination thereof. Such instructions may specify the frequency the food items and tagging agent are to be consumed by an individual over time.

The instructions may also include, for example, instructions for coordinating the dietary regimen for use together with one or more doses of a tagging agent. For instance, certain tagging regimens involve drinking specific volumes of tagging agent over a 24-hour period. Thus, the instructions may specify, for example, the volume of tagging agent to be consumed over time in conjunction with the nutritional dietary regimen. For example, the instructions may provide that one dose of tagging agent be consumed in the morning, and one dose in the afternoon, and one dose in the evening prior to a predetermined medical activity, such as a medical diagnostic procedure.

The present invention may also provide a container structured to allow for placement of the food items and the coordinating instructions. This enables each of the food items to be placed in the kit, thus making the present system easy to follow, which facilitates user compliance. A non-limiting example of such a container is shown in FIG. 1. In FIG. 1, container (1) contains multiple food items of the present invention. Specifically, nutritional drink (2) is positioned in section (3) located at the front of container (1). A first snack food (4) is positioned in adjacent section (5). Another nutritional drink (6), along with a beverage (7) and soup product (8) is positioned in section (9). A second snack food (15) is positioned in subsequent section (10). In one embodiment of the present invention, the snack food (4) or (15) may comprise a starch food, protein supplement, fruit food or vegetable food. Another nutritional drink (11), beverage (12) and grain food (13) is positioned in the farthest section (14) relative to the front of the container.

Indicia may be included in at least one of the surfaces of the container and/or one or more food items. The indicia may take the form of a writing or illustration or both, to assist the individual to readily distinguish the food items from each other. This feature is especially useful for individuals that are ill, weak or suffer from poor vision, or that experience difficulty in reading labels found on ordinary food containers. In one embodiment of the present invention, the indicia may comprise large lettering or illustrations readily in identifiable colors.

Figure 5:
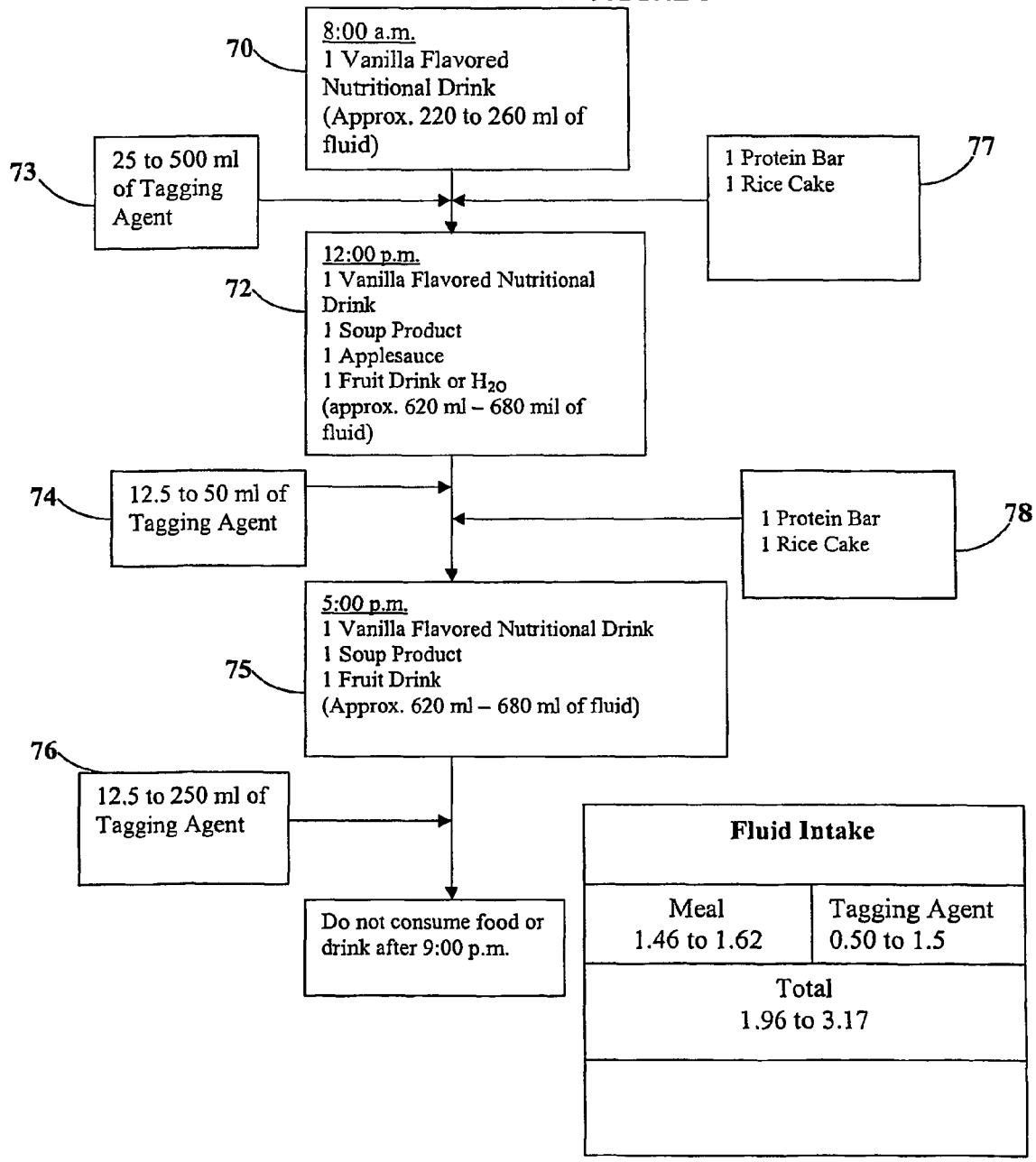
FIG. 5 is a non-limiting diagram of an alternative embodiment of the present invention.

FIG. 5 shows an alternative embodiment wherein the dietary regimen of the present invention is used in conjunction with a tagging regimen. A first feeding (70) is consumed in the morning, for example, at about 8:00 a.m. The first feeding may comprise one nutritional drink. It may also comprise 3 to 5 oz of boiled white rice and 200 ml to 250 ml, such as a water or a fruit drink. A first dose of tagging agent (73) may be consumed thereafter. A second feeding (72) may be consumed at or about mid-day, for example at 12:00 p.m. Second feeding (72) may comprise one soup product, one nutritional drink and one beverage. After the second feeding, the individual may consume a second dose of tagging agent (74). A third feeding (78) may be consumed at about late afternoon or early evening, at about 5:00 p.m., for example. Third feeding (78) may comprise one soup product, one nutritional drink and one beverage. After the third feeding, the individual may consume a third dose of tagging agent. First and second snacks (77, 78) may be consumed between the first and second feeding (70, 74), and second and third feedings (72, 75), respectively. Each snack may comprise one or more protein supplements or starch foods. Such snacks may also comprise a soup product, grain food, and fruit or vegetable food.

Figure 2:
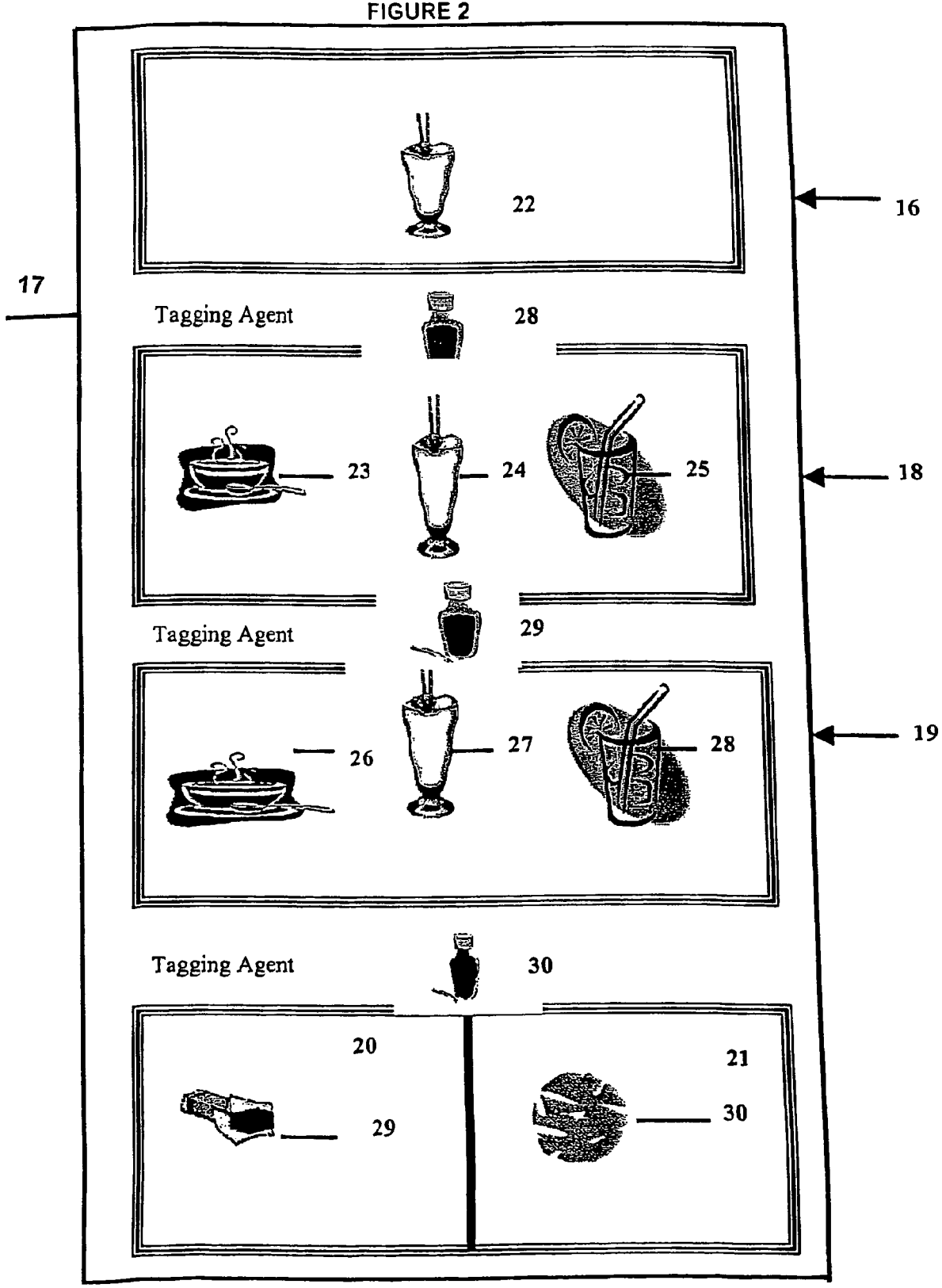
FIG. 2 is a non-limiting example of a kit comprising the food items of the present invention, along with one or more doses of a tagging agent.

In reference to FIG. 2, a representative kit of the present invention is shown comprising three feedings. A first feeding (16) is placed in one portion of the present invention (17), a second feeding (18) is placed in an adjoining section of kit (17) and a third feeding (19) is placed in adjoining section (17). Also, two food items, first snack (20) and second snack (21) are placed in an adjacent divided area (17). In this embodiment, the present invention comprises approximately 2000 calories. Three doses of tagging agent (28-30) may also be placed in kit (17). However, it is understood that the kit may contain one or more doses of tagging agents, or none. Instead, tagging agent may be produced separately.

In FIG. 2, each feeding represents consumption of one or more food items. For example, the first feeding may comprise one nutritional drink (22). The second feeding may comprise one soup product (23), one nutritional drink (24) and one beverage (25). The third feeding may comprise one soup product (26), one nutritional drink (27) and one beverage (28). The first and second snacks (20, 21) may comprise one protein supplement (29) and one starch food (30), respectively. These items may be consumed between the first and second feedings, and second and third feedings, respectively.

Figure 3:
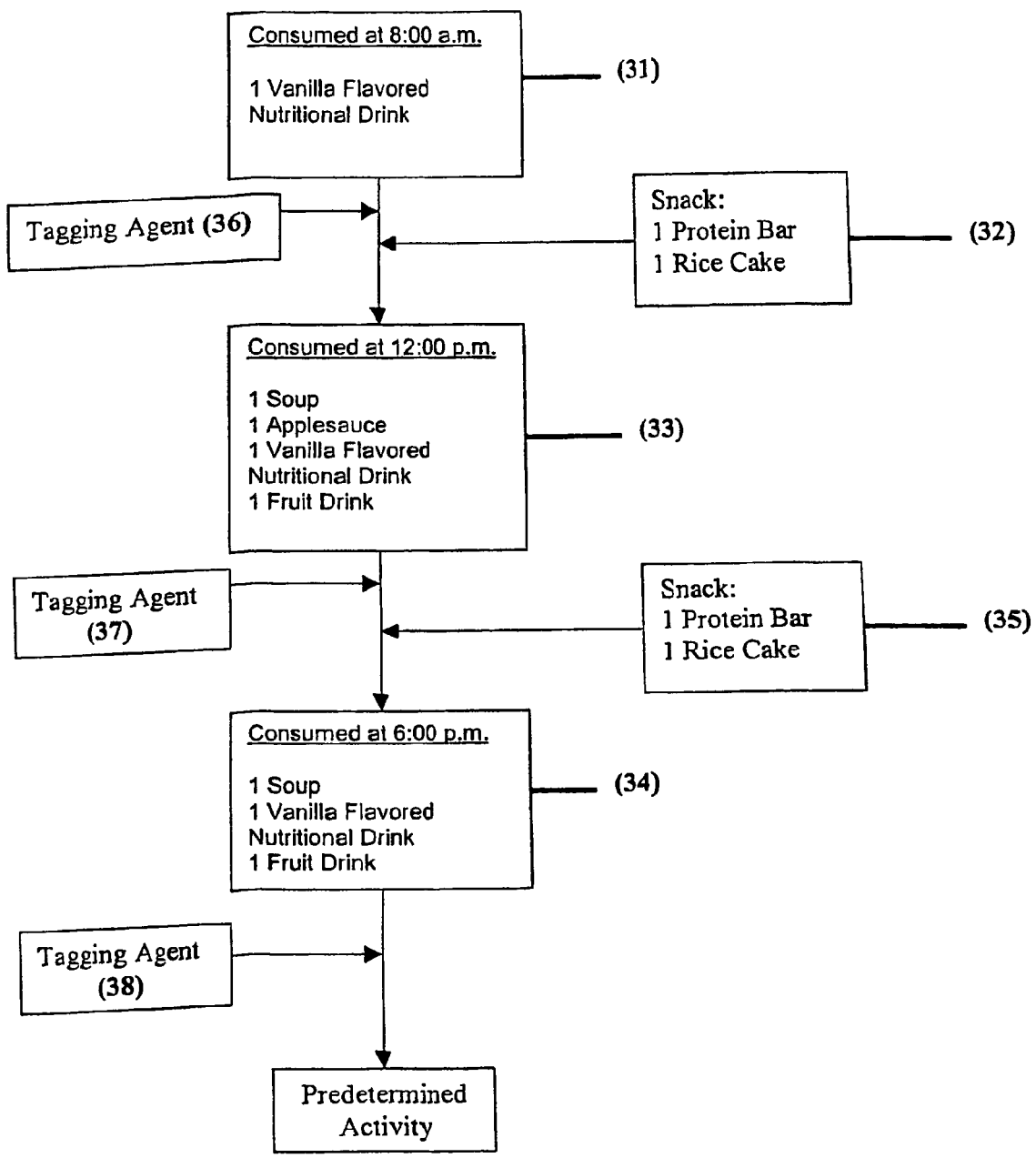
FIG. 3 is a non-limiting diagram of a dietary regimen and tagging regimen of the present invention.

In reference to FIG. 3, the method/system or kit of the present invention may contain one or more food items arranged into three meals. The first feeding (31) is consumed, for example, at about 8:00 a.m. and may comprise one nutritional drink. A first dosage of tagging agent (36) may be consumed thereafter. A first snack (32) may be provided, and first snack (32) may comprise one protein supplement and/or one starch food. The second feeding (33) may be consumed at about 12:00 p.m. and may comprise one soup product, one nutritional drink, one fruit food and one beverage. A second dosage of tagging agent (37) may be consumed after. The third meal (34) may be consumed at about 6:00 p.m. and may comprise one soup product, one nutritional drink and one beverage. A third dosage of tagging agent (38) may be consumed thereafter. A second snack (35) may be provided, and snack (35) may comprise one protein supplement and/or one starch food. First and second snacks (32, 35) may be consumed between the first and second feeding (31, 33), and second and third feedings (33, 34), respectively.

Also, the first, second and third feedings (31, 33, 34) may represent a breakfast, lunch and dinner meal, respectively. For example, in reference to FIG. 5, breakfast meal (36) may be placed in one portion of a kit (37), a lunch meal (38) may be placed in an adjoining section of kit (37), a dinner meal (39)

may be placed in adjoining section of kit (37) and lastly the two snack items, i.e., first snack (40) and second snack (41), may be placed in an adjacent divided area of kit (31). In this embodiment, the whole kit comprises approximately 2,000 calories and may be consumed over about a 24-hour period.

In another embodiment, the present invention is a method for use in preparing an individual for a predetermined activity. Such is accomplished by providing the individual one or more food items and tagging agents for consumption prior to a predetermined activity. The present invention may also be carried out by instructing the individual to obtain items, individually or collectively, and consume them. For example, a physician may instruct an individual to prepare, purchase or otherwise obtain the one or more food items and doses of tagging agents, individually or collectively, and instruct the individual to consume these items prior to a predetermined activity and/or pursuant to a regimen.

In another embodiment, the method of the present invention comprises the step of providing an individual one or more doses of tagging agent and one or more food items arranged in three separate feedings. The method may also comprise the step of instructing the individual to prepare, purchase or otherwise obtain the necessary food items, individually or collectively, to compose these feedings, and consume them pursuant to a predetermined dietary regime and/or prior to a predetermined activity.

In another embodiment, the method of the present invention comprises the step of providing an individual one or more doses of tagging agent and one or more food items arranged into three specific types of feedings, particularly a breakfast feeding, a lunch feeding and a dinner feeding.

Figure 4:
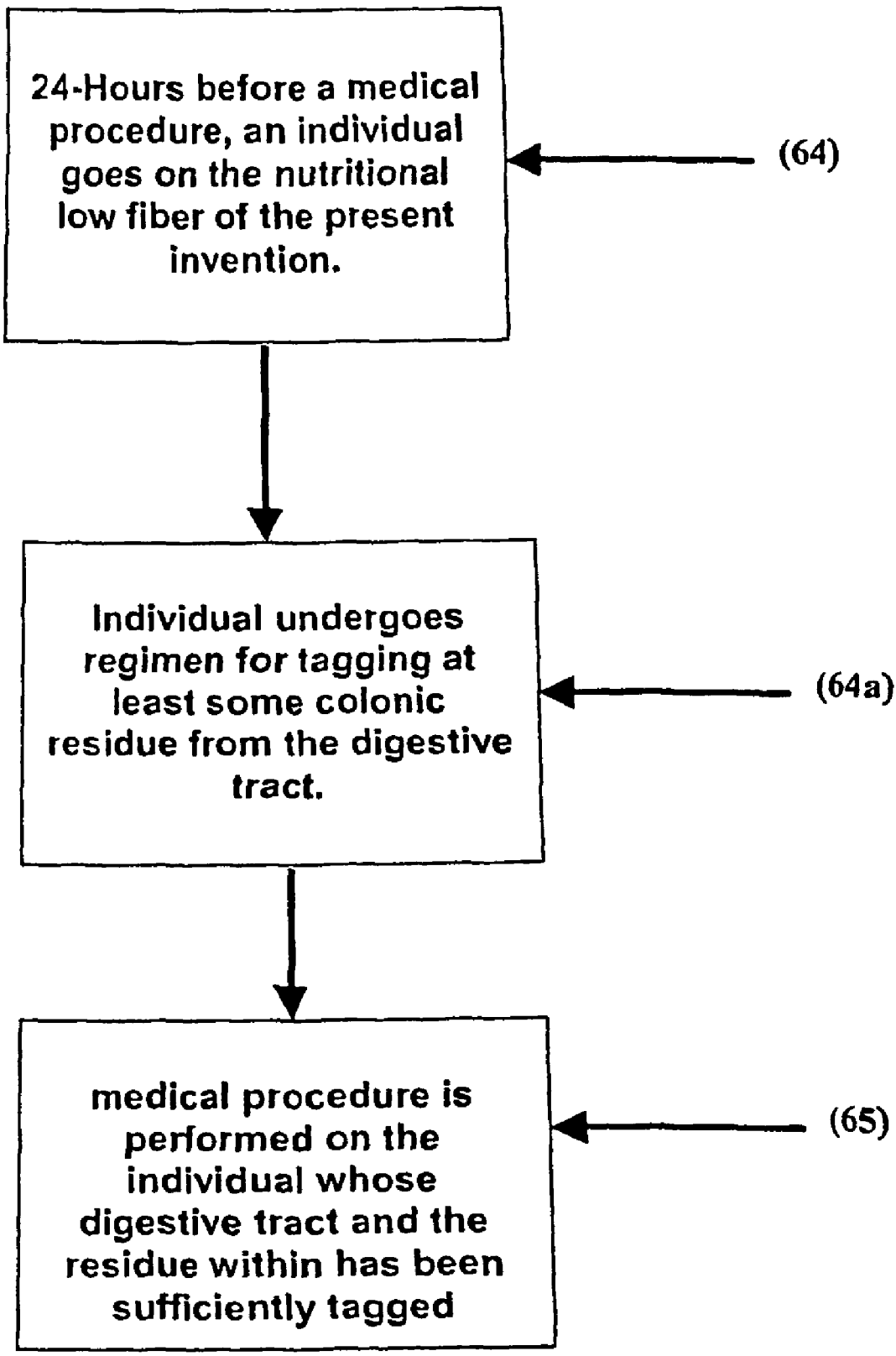
FIG. 4 is a non-limiting diagram of an alternative embodiment of the present invention.

In reference to FIG. 4, a non-limiting embodiment of the method of the present invention is disclosed. First, step (64) involves having an individual undergo the diet of the present invention approximately twenty-four hours, or one day, before a predetermined activity, including but not limited to, a diagnostic procedure such as colonoscopy. Step (64a) involves the individual undergoing a regimen for tagging at least some colonic residue in removing food residue from the digestive tract. Step (65) involves having the colonoscopy performed approximately 24 to 36 hours after step (64). In step (65), the colonoscopy is successful because the stool was sufficiently tagged, such that it could be differentiated from surrounding tissues.

Further, in reference to FIG. 4, in step (64) the individual does not experience the detrimental effects that are commonly associated with the clear liquid diet known in the prior art, e.g., symptoms of lightheadedness and dizziness due to insufficient calories and nutrition.

first and second feeding (31, 33), and second and third feedings (33, 34), respectively.

Figure 6:
FIGS. 6-12 are radiographic images of a cross section of an abdomen, including portions of a colon, illustrating an example of the type of stool marking that would be present when an individual's digestive tract is prepared in accordance with the present invention.
Figure 7:
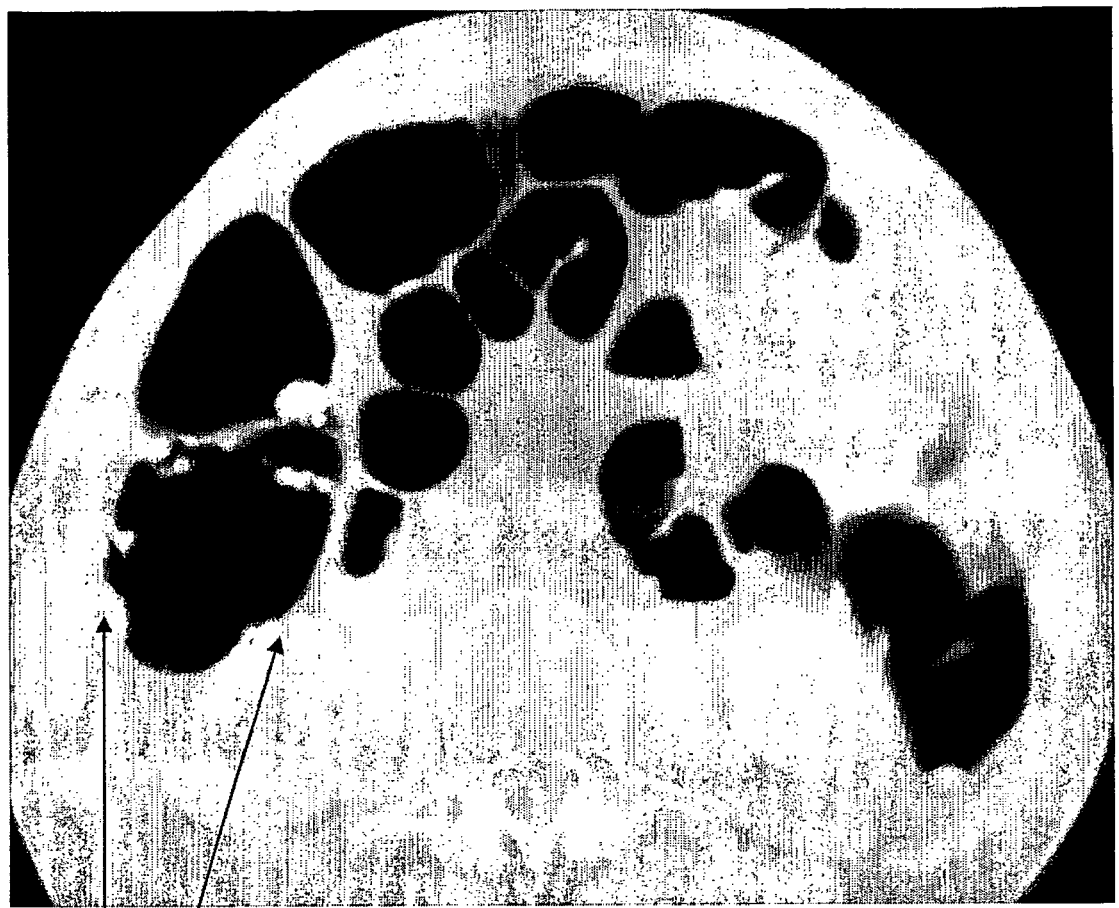
Figure 8:
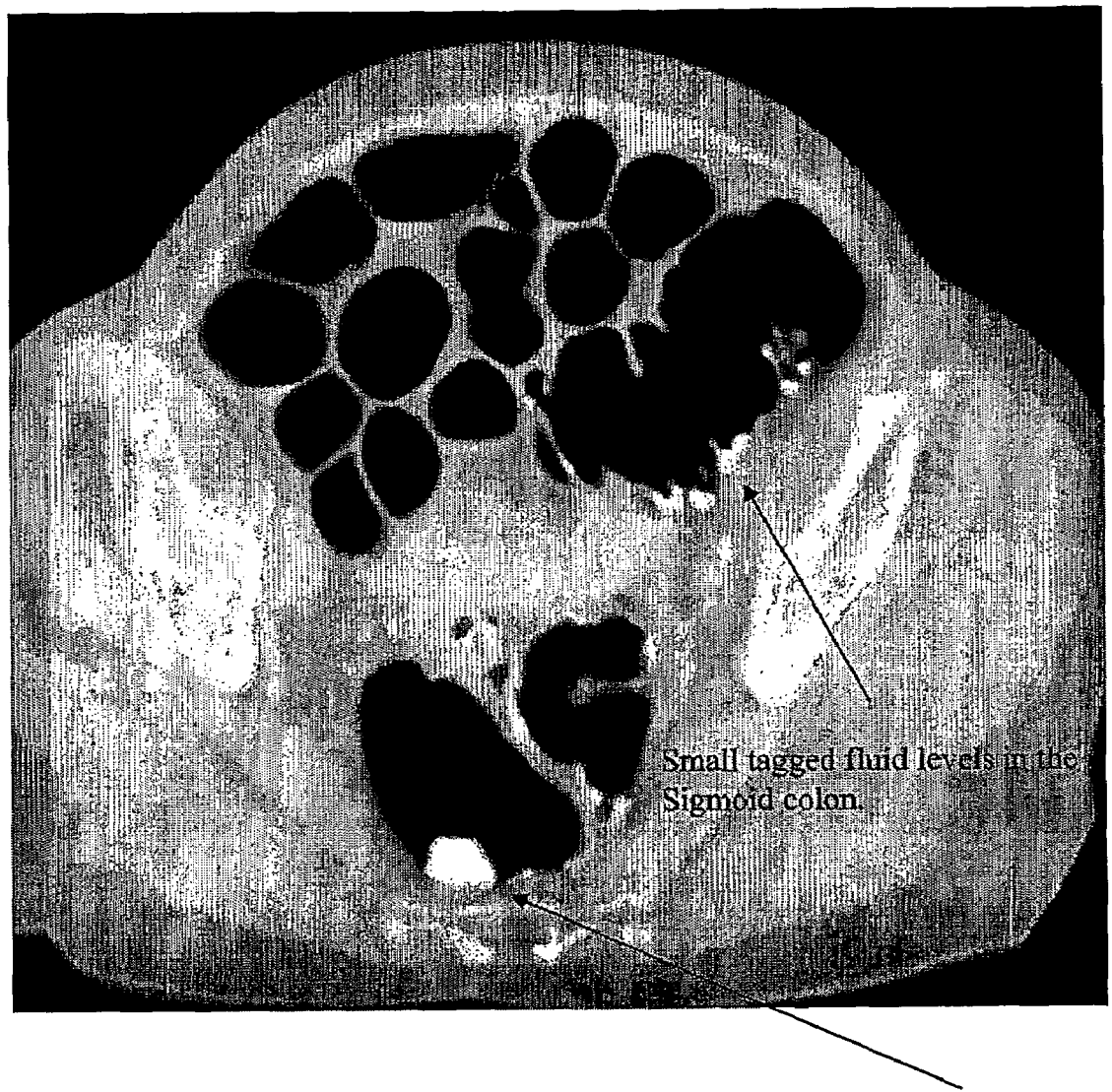
Figure 9:
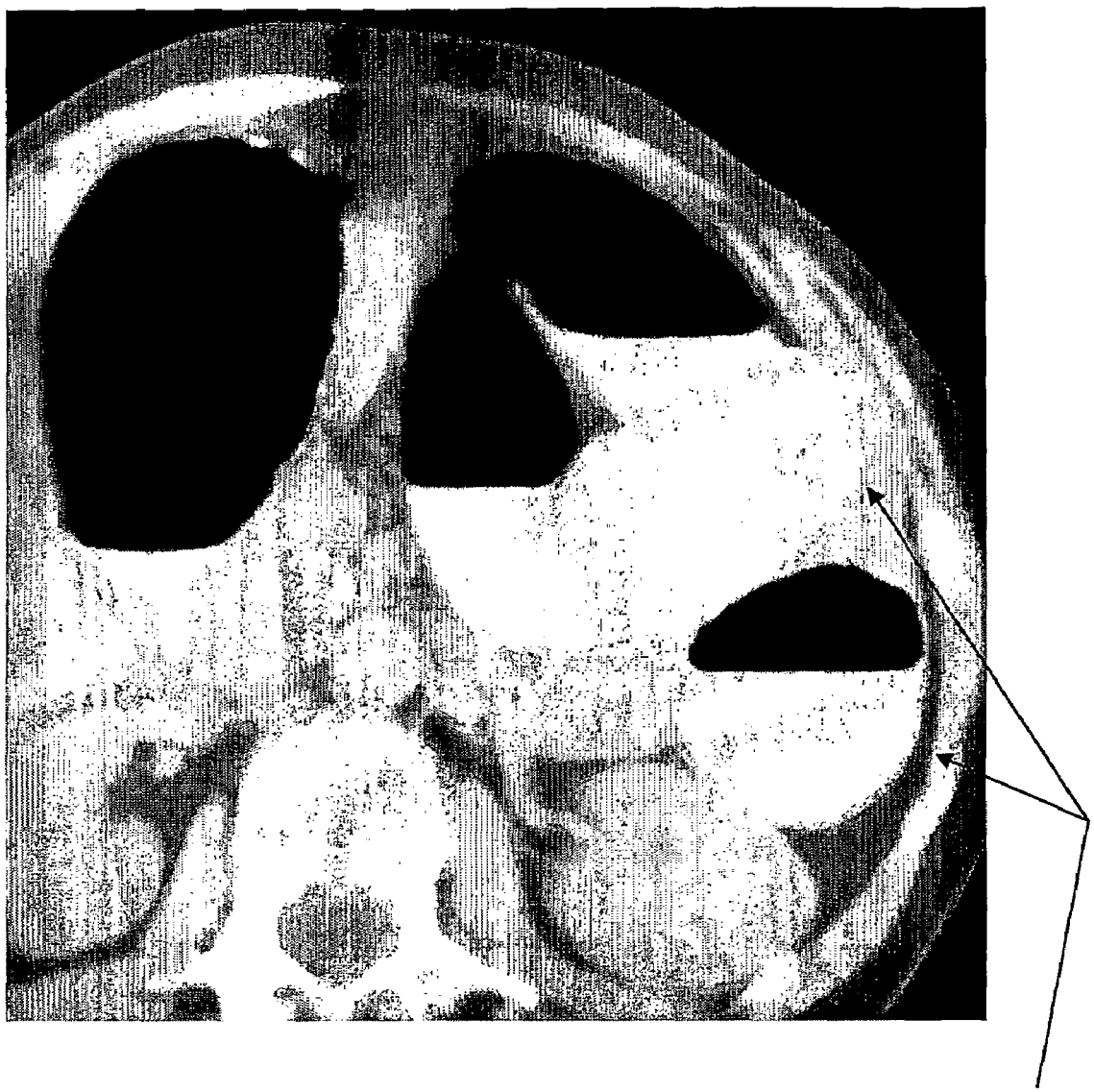
Figure 10:
Figure 11:
Figure 12:

FIGS. 6 to 12 illustrate a single slice CT scan (Philips AV/FU) of an individual's colon. For each figure, the slice thickness is 5 mm, table increment is 7 mm, and the reconstruction index is 2 mm. Specifically, FIGS. 6 to 8 are colonography images of an individual receiving 3 doses of tagging agent over a 24-hour period. The doses were 25 ml, 12.5 ml, and 12.5 ml comprising 40% w/v barium sulfate. The individual underwent a bowel cleansing prior to the colonography procedure. FIGS. 9 through 10 are also colonography images. In FIG. 9, the individual was administered 3×250 ml doses of 2.1% w/v barium sulfate over a 24-hour period. Also, the individuals underwent bowel cleansing prior to the colonography. In FIGS. 11 to 12, the individuals were administered 3×250 ml doses of 2.1% w/v barium sulfate over a 24-hour period. During that time, the patient underwent a low residue diet, in accordance with the present invention. Also, the individuals' fluid intake was limited to 1.5 to 2.0 liters. Here, the individuals did not undergo a bowel cleansing prior to the colonography procedure.

Generally, in evaluating radiographic images, the radiologist has to interrogate the data set produced by such images. The radiologist typically reviews the images at a workstation. In some instances, the images will be displayed in a 2D axial format. In using the present invention, the radiologist can differentiate between retained stool and a polyp due to the presence of tagging agent in the stool. One of the values of the present invention is the contribution of creating a setting where the differentiation between stool and an abnormal finding (e.g., polyp) is readily apparent and does not require extensive time and effort to examine. Further, the radiologist can screen the radiography image to identify the presence of any abnormalities without manipulating the images (e.g., electronically removing the marked stool from the images). This is because the stool is thoroughly marked, and the usual features of the marked stool are readily distinguishable from those of the soft tissue. Consequently, the radiologist spends less time to evaluate images of colons prepared by the present invention, allowing him/her to spend more time on other issues that require their expertise in imaging interrogation. The reduction of time to review the images also equates to less "eye strain" by the radiologist improving their overall performance and productivity.

Also, the development of Computer Assisted Differentiation (CAD) systems will be able to utilize the tagging regime of the present invention. For example, the images of the colons prepared by the present invention can strengthen the CAD algorithms to differentiate between retained residue and colonic anomalies. For instance, the tagged stool can be incorporated in the algorithm or subtracted out of the image for CAD review.

VII. EXAMPLES

The invention may be further understood by a consideration of the following examples, which are intended to be purely exemplary of the use of the invention.

Example 1

The following study evaluated the use of barium as the sole tagging agent in the context of prep less CTC. In a Patient Study I, the range of highest densities in the fecal residue using barium as the sole tagging agent in combination with reduced cathartic cleansing was evaluated. In Patient Study II of the study the assumptions derived from these findings were evaluated in a phantom study. Finally, based upon these observations, we developed a method of labeling stool with barium as the sole tagging agent in the unprepped colon. In the perspective of electronic cleansing, it was the objective to obtain a sufficiently high density of the tagged stool and a sufficiently dry colon.

Patient Study I

A comprehensive test of the invention was performed on 100 patients who had undergone CTC after a dedicated preparation. Two days before the procedure, the patients were asked to observe a classic low residue diet. The day before the examination, patients had three meals breakfast, lunch and dinner) with a dedicated low residue diet (Nutra Prep, E-ZEM, Westbury, N.Y., USA) in order to perform nutritional bowel cleansing. At each meal 250 ml of a 2.1% barium solution (Tagitol, E-Z-EM) was administered. The maximal fluid intake was 3 to 3.5 liters for that day. The patients were however not obliged to follow the proposed hydration regimen. After dinner, cathartic cleansing of the colon was performed using magnesium citrate and four Bisacodyl tablets. On the morning of the examination, patients were asked to insert a Bisacodyl suppository. No breakfast was allowed on the day of the examination. CTC was performed in the morning. After relaxation with scopolaminebuthylbromide (Buscopan, Boehringer Ingelheim, Paris, France) and inflation of the colon with room air, single slice helical CT of the colon was performed with a slice thickness of 5 mm, a 7 mm table feed and a 3 mm reconstruction index. Patients were scanned in supine and prone position. Two radiologists (P. L. and S. G.) reviewed all CTC. Age, gender, examination date and colon length were recorded. The colon length was measured using central path tracking. In case of collapse or spasm of a colonic segment the path was continued through the collapsed zone. Each colon was reviewed in order to assess the amount of residual stool and fluid and the efficacy of tagging. The residual stool was measured and divided in 3 categories according to size, the largest size having priority over the smaller sizes (1=<5 mm; 2=6 9 mm; 3=>10 mm). In accordance with the protocol set forth in Macari et al., Radiology 2001; 218: 274-277, the amount of fluid was measured according to its proportion to the maximum anteroposterior diameter of that segment of the colon in which it was detected (1=0% of the lumen; 2=<25%; 3=25-50%; 4=>50% of the lumen). On each occasion density measurements (H.U.) of the residual stool and fluid were performed. Since the purpose of the study was to evaluate the range of highest densities obtained with barium as the sole tagging agent, ROI density measurements of the visually best tagged residue were obtained. This was done on a segmental basis.

Phantom Study

A plastic bottle with a diameter of 5.5 cm and filled with a 2.1% watery barium suspension was submerged into a plastic box filled with water. This phantom was scanned along its longitudinal axis each 24 hours, using the scanning parameters detailed above. In this way circular sections of the bottle with the barium suspension were obtained. On each occasion, densities were measured on the axial slices using a circle covering the entire surface of the section of the bottle except for a peripheral 1 mm ring to avoid partial volume averaging. At each time a histogram was obtained indicating mean, maximum and minimum density values and the standard deviation (H.U.). These measurements were compared. The measurements were suspended when there were no significant changes in densities after 2 consecutive measurements.

Patient Study II

A comprehensive test of the invention was also performed on 3 groups of 3 patients, who underwent CTC after a dedicated preparation. All patients were asked to observe the dedicated low residue diet the day before CTC as described above. In all groups a strict hydration regimen was followed. In group 1, the beverage consisted of 250 ml of a 2.1% barium suspension at breakfast, lunch and dinner. An additional 750-1250 ml of water could be ingested. No fluid intake was permitted after 8 o'clock p.m. In group 2, patients took in 250 ml of a 4 barium suspension at breakfast and 250 ml of a 2.1% barium suspension at lunch and dinner. The same amount of additional beverage was allowed as in group 1. In group 3 nutritional cleansing started with 3 aliquots of 50 ml of a 4% barium suspension at breakfast, lunch and dinner 2 days before CTC. The day before CTC, the same regimen as in group 1 was followed. There was no cathartic bowel cleansing in any of the patient groups. In all groups CTC was performed using the same method as in patient study I. The residual stool and fluid were evaluated as in study I. In all patients, density measurements were performed of all residue.

Results

Patient Study I

There were 43 female and 57 male patients with ages varying from 36 to 90 and with a mean age of 63. Colon length varied from 126 to 231 cm with a mean length of 164 cm. In total 600 colonic segments were examined.

1. Fecal Residue.

No significant relationship between demographic data, colon length, examination date, colon cleanliness, and density of fecal residue or fluid was detected.

a. Quantity and Size.

In 14 patients, no fecal residue was detected. Fecal residue was detected in 217 segments (36.2%) of 86 patients. These fecal residues were mostly right-sided: Cecum: 66 segments; ascending colon: 59 segments. Residue >10 mm were observed in 24 segments (4%). Fecal residue 6-9 mm was detected in 60 segments (10%). In 133 segments (22%) only residue <5 mm was detected.

b. Efficacy of Tagging.

In 7 patients (9 segments) non-tagged fecal residue was found, with 5 segments having stool 6-9 mm and 2 segments with stool >1 cm.

Density measurements of the tagged stool revealed a very wide range of densities from 20 H.U. up to 2890 H.U. The mean highest densities (H.U.) and standard deviations are listed in the table below.

|  | Stool Size | | |
| --- | --- | --- | --- |
|  | >1 cm | 6-9 mm | >5 mm |
| Highest mean density | 863 SD 800 | 540 SD 533 | 268 SD 224 |

In 59 segments (9.8%), representing 33 patients, at least one fecal residue with a density of >500 H.U. was detected. These residues were mostly right-sided: Cecum: 16; ascending colon: 17; transverse colon: 16.

2. Residual Fluid.

Residual fluid was detected in 82 patients representing 272 colonic segments (45.3%)(Cecum: 66; ascending colon: 64; transverse colon: 52; descending colon: 50; sigmoid colon: 28; rectum: 12). In 50 of these segments over 25% of the colonic lumen was covered on at least 1 axial slice. The residual fluid never reached a density >500 H.U. No more than 5 patients (5 segments) had a fluid level with a density >400 H.U. There were non-tagged fluid levels in 70 colonic segments (34 patients). Only in 3 patients this non-tagged fluid level covered more than 25% of the colonic lumen on at least one axial slice.

Phantom Study

The changes in the phantom were observed during an 8 week time span. At the start the barium suspension in the bottle was homogeneous with a mean density of 400 H.U. Gradually the barium barium settled towards the bottom of the bottle ending as a dense layer with a maximum density of 2895 H.U. In the top of the bottle the barium suspension became less dense and ended up as a watery solution with a minimum density of 6 H.U in the top. There was no change of the mean density of the solution.

Patient Study II

In all patients the ceco-ascending colon presented with fecal residue. The descending colon, the sigmoid and the rectum were empty in 4, 5 and 3 patients respectively. In all segments there was at least 1 residue >10 mm. The largest amount of fecal residue was located in the ceco-ascending colon.

Efficacy of Tagging

The mean highest densities of the tagged stool (H.U.) and standard deviations are listed in the table below.

|  | >1 cm | 6-9 mm | >5 mm |
|---|---|---|---|
| Group 1 | 1161 SD 208 | 937 SD 135 | 616 SD 120 |
| Group 2 | 1390 SD 111 | 1450 SD 126 | 872 SD 96 |
| Group 3 | 1852 SD 353 | 1483 SD 98 | 1125 SD 65 |

In 2 patients (group 2 and 3) there were some very small (<5 mm) non-tagged residues in the right hemi colon. Two patients presented with non-tagged residue of 1 cm in the rectum. This stool contained air and was surrounded by a barium ring.

Residual Fluid.

In 3 patients there was a very small fluid level (less than 10% of the colonic lumen). In all cases this fluid was located in the Cecum. It concerned 2 patients from group 2 and 1 from group 3. These fluid level had a density of 390, 360 and 420 H.U. respectively.

In patient study I, the efficacy of fecal tagging using barium as the fecal tagging agent in combination with a low residue diet and cathartic cleansing based on magnesium citrate was assessed. The present invention performs efficacious tagging despite the use of a milder cleansing regimen when compared to the cathartic cleansing used in CT colonography. The present method resulted in an increased patient compliance (Lefere P A, Gryspeerdt S S, MD, Dewyspelaere J, Baekelandt M, Van Holsbeeck G B. Dietary fecal tagging as a cleansing method prior to computed tomographic colonography: initial results—polyp detection and patient acceptance. Radiology 2002; 224: 393-403).

In patient study II the cathartic cleansing was omitted during the preparation process. Here, a combination of a low residue diet and a hydration control regimen was administered the day before CT colonography. Tagging based on a 2.1% barium suspension resulted in adequate stool tagging. It is evident that the omission of the cathartic cleansing resulted in an increased patient compliance.

Example 2

Fifteen volunteers were scheduled for regular abdominal CT. There were 3 male and 6 female patients. The age ranged between 23 and 73 years (mean age: 55.7 years). All patients suffering from vague abdominal pain. According to their preparation, the patients were divided in 2 sections.

1. Section One.

The first section consisted of 9 patients. All patients were prepared with a dedicated low residue diet presented in a single kit (Nutra Prep, E-Z-EM, Westbury, N.Y., U.S.A.). This diet was designed conceived to perform nutritional bowel cleansing in order to control fat intake and to decrease fecal output. It contained: vanilla flavour shake, fruit juice, soup, apple sauce, potato poppers and nutrition bars. The patients began the diet in the morning of the day before the examination. At breakfast, the patients consumed the vanilla flavour shake (about 250 ml). Patients could choose one more drink (about 250 ml) in the morning. At lunch, the patients ingested another 250 ml of liquid (vanilla flavour shake, fruit juice or soup). They were also allowed to have a supplementary drink (about 250 ml) in the afternoon. At dinner, the patients consumed another 250 ml drink (vanilla flavour shake or soup). The patients were instructed not to consume any more liquids. This resulted in a fluid intake ranging between 750 ml. and 1250 ml. The patients were not required to eat all the contents of the preparation kit.

Fecal tagging was performed with barium (Tagitol, E-Z-EM, Westbury, N.Y., U.S.A.). Three different regimens of barium intake were followed. Here, the patients were divided in 3 groups of 3 patients (Table 1). Group 1 took in 250 ml of a 2.1% barium suspension at breakfast, lunch and dinner. Group 2 ingested 250 ml of a 4% barium suspension at breakfast, followed by 1 dose of 250 ml of the 2.1% suspension at lunch and dinner. Group 3 ingested barium over 2 days. Here, two days before the exam, the patients ingested 3 doses of 50 ml of the 4% barium suspension. On that day, they were allowed to consume their usual meals. The day before the examination, they followed the same tagging regimen as in group 1. This combination of fluid and barium intake resulted in a total fluid intake ranging between 1.5 and 2 liters the day before the examination. Patients were not allowed to drink more nor to have any drinks after 9 p.m. that day. There was no cathartic cleansing in any of the patient groups. The morning of the examination the patients could not consume anything by mouth.

2. Section Two.

This section consisted of two groups of three patients. All patients were prepared with a dedicated low residue diet presented in a single kit (Nutra Prep, E-Z-EM, Westbury, N.Y., U.S.A.). This diet was conceived to perform nutritional bowel cleansing in order to control fat intake and to decrease fecal output. It contained: vanilla flavour shake, fruit juice, soup, apple sauce, potato poppers and nutrition bars. The diet was started in the morning of the day before the examination. At breakfast, the patients consumed the vanilla flavour shake-shake (about 250 ml). They could also have a cup of decaffeinated coffee (about 200 ml). Patients could choose to have 2 more drinks (about 500 ml) in the morning. At lunch, they ingested another 250 ml (vanilla flavour shake, fruit juice or soup). They were also allowed to have 2 supplementary drinks (about 500 ml) in the afternoon. At dinner they had another 250 ml drink (vanilla flavour shake or soup). After this they were not allowed to consume any more liquids. This resulted in a fluid intake ranging between 1450 and 1950 ml. The patients were not required to eat all the contents of the preparation kit.

Fecal tagging was performed with barium diluted at 40% weight/volume. Two different regimens of barium intake were used. Accordingly, the patients were divided in two groups of three patients (group 4 and 5). The day before CTC, group 4 took in 25 ml of the barium suspension at breakfast and 12.5 ml at lunch and dinner respectively. This resulted in 50 ml of barium intake for that day. Group 5 started their intake of barium two days before CTC with 12.5 ml at breakfast, lunch and dinner respectively. The next day they followed the same barium regimen as group 4.

All patients were examined with a 5 mm slice thickness, a 7 mm table feed (pitch about 1.4), and a 3 mm reconstruction index. This resulted in an effective slice thickness of 7 mm. Scans were obtained at 100 mAs and 120 kV. The obtained images were sent to a workstation (EasyVision, Philips, Best, The Netherlands). In each patient the colon was reviewed in order to assess the amount of residue and the efficacy of tagging. The colon was divided in 6 segments: cecum, ascending colon, transverse colon, descending colon, sigmoid colon, rectum.

A. Amount of Residue

To evaluate the amount of residue 3 different entities were considered: (1) the residual stool; (2) the fluid; and (3) the barium layer. This residual stool was evaluated and divided in 3 categories according to its size (0=no residual stool, 1=residual stool ≦5 mm, 2=residual stool 6-9 mm, 3=residual stool ≧10 mm). To evaluate the quantity of the residual stool, the number of stool balls was evaluated in each segment. (A=empty, B=1-10, C>10). The fluid was defined as a classic horizontal air-fluid level in the dependent part of the colon with a meniscus at its junction with the colonic wall. In observation of Macari et al., the amount of fluid was assessed on a 1 to 4 basis according to its proportion to the maximum anteroposterior diameter in that segment of the colon it was detected (1=0%, 2=<25%, 3=25-50%, 4=>50% of the lumen). At the same time the number of slices with fluid was recorded for that segment. The barium layer was defined as a layer of barium moulded over the haustrations and semi-circular folds, evenly distributed on the dependent and non-dependent colonic border, without the classic air-fluid level and without meniscus at its junction with the colonic wall. Segmental evaluation of this barium film was performed. According to its thickness, the barium layer was divided in the same categories as the residual stool (0=no barium film, 1=thickness ≦5 mm, 2=thickness 6-9 mm, 3=thickness ≧1 cm)

B. Efficacy of Tagging

To evaluate the efficacy of tagging two methods were used. First, according to Callstrom et al. (19), all residue (i.e. residual stool, fluid, barium) with a density ≧150 H.U. was electronically labeled (green) on the axial slices. For each axial slice the same subjective visual labeling score of 0%, 25%, 50%, 75% and 100% was used with 0% being non-tagged residue and 100% being completely tagged residue. This score was evaluated per segment. Second, density measurements (Hounsfield Units (H.U.)) of the residue (i.e. fecal residue, fluid, barium film) were performed in all patients on a per-size basis. The effective slice thickness being 7 mm, only densities of residue ≧7 mm were measured. This was done to avoid partial volume averaging.

For residue ≧7 mm a region of interest (ROI) was used. According to Swensen et al., this ROI was round or oval according to the shape of the residue. In order to avoid partial volume averaging a 2 mm peripheral border was not included in the ROI. At each time the mean density, maximum and minimum values and the standard deviation were recorded the mean values of all measurements (i.e. mean density, maximum and minimum density, standard deviation) were calculated per patient and per segment. Per patient group the range of the minimum density values (lowest and highest minimum) was recorded. All density measurements were performed on bone-window images.

Results

A total of 90 segments were reviewed. The results concerning the size and quantity of the residual stool are listed in table 2 and 3 respectively.

A. Section One: There were 13 segments (24.07%), representing 6 patients, without residual stool. Patient 5 presented without fecal residue. In 6 patients, there were 8 segments (14.8%) with only residual stool ≦5 mm. In 29 segments (53.7%) of 8 patients the colon presented with more than 10 pieces of stool. There were 22 segments (40.7%) presenting with over 10 pieces of residual stool and with residual stool ≧1 cm. Of these segments, 10 (18.5%) were located in the ceco-ascending colon and 4 (7.4%) in the rectum.

B. Section Two: There were 12 segments (33%), representing 5 patients, without residual stool. There were 3 segments (8.3%) with only stool ≦5 mm. In 18 segments (50%), representing 5 patients, there were more than 10 pieces of stool. There were 25 segments (69.4%) presenting with over 10 pieces of residual stool and with residual stool ≧1 cm.

The results concerning the fluid levels are listed in table 4. Regarding Section One, 3 patients had a fluid level covering less than 25% of the colonic lumen. At each time this fluid level was located in the cecum (3 segments about 5.5%). It concerned 2 patients from group 2 and 1 patient from group 3. In Section Two, there was a fluid level in 5 segments. In 4 segments the fluid covered less than 25% of the colonic lumen. In the other segment, this fluid was located in the rectum and covered more than 50% of the lumen.

The results concerning the barium film are listed in table 5. In Section One, 7 patients provided a total of 18 segments (33.3%) with a barium film. In 8 (14.8%) segments the barium layer had a thickness of only ≦5 mm. Patient 5, who presented without fecal residue, had a barium film in all but one segment. Taking into account the fecal residue, the fluid and the barium film, 5 segments (9.25%) were completely empty and 2 segments (3.7%) presented with only a barium layer ≦5 mm. In 7 segments (13%) there was only residue ≦5 mm. This means that in total 14 segments (25.9%) were quite clean (Table 6). In Section Two, 5 patients provided a total of 10 segments with a barium film. This barium film covered less than 5 mm in 3 segments. Taking into account the fecal residue, the fluid and the barium film, 5 segments (%) were completely empty. In 3 segments (8.3%) there was only residue ≦5 mm. This means that in total 14 segments (38.8%) were quite clean (Table 6).

B. Efficacy of Tagging

Figure 13:
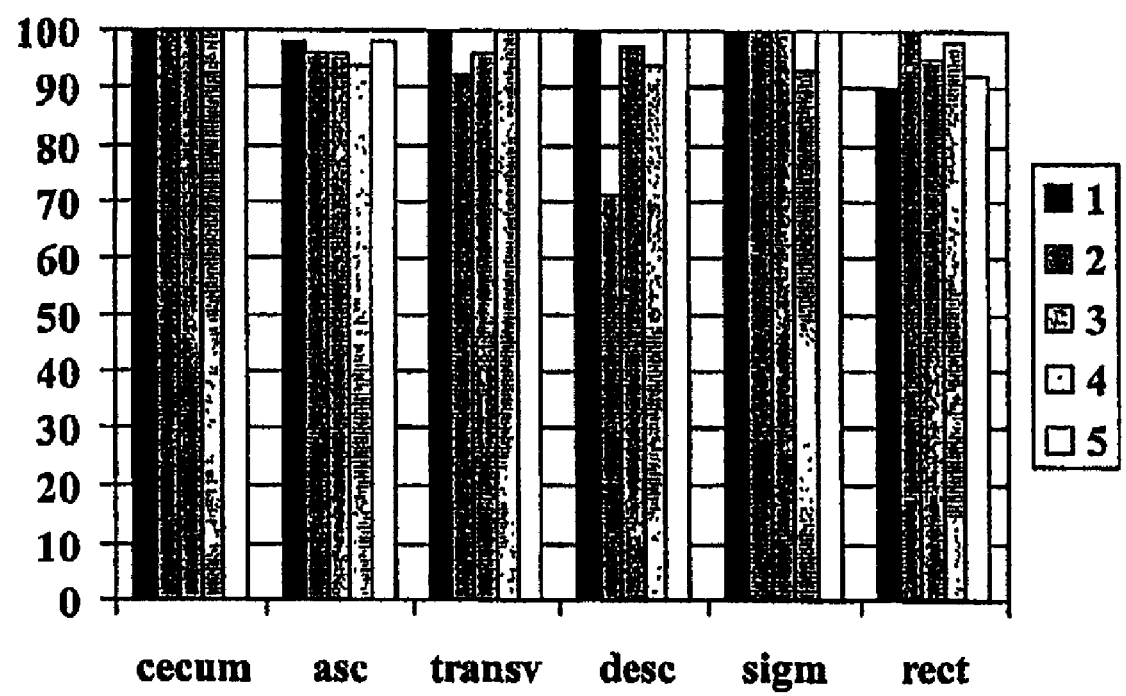
FIG. 13 is a non-limiting example of a graph illustrating the results of the visual labeling score of the stool.

In total 486 ROI density measurements were performed. The results of the visual labeling score of the stool are shown in FIG. 13. These scores varied between 90 and 100% for all groups, except for the descending colon in group 2, where a score of only 71% was obtained. In this group one patient (patient 4) presented only with stool ≦5 mm in the descending colon. This stool was not electronically labeled although the residue appeared as tagged on a visual basis. In this patient the score for the descending colon was only 20%. Two patients presented with a 1 cm non-tagged residue in the rectum. This non-tagged stool was easily recognizable as it contained air and was completely surrounded by a barium ring. The results of the ROI density measurements for residue ≦7 mm are listed in table 8. High densities were obtained in all segments of all patients. The fluid levels had densities of between 360 and 420 H. U.

TABLE 1

This table illustrates the different regimen of barium intake.

| | 2 Days before CTC | | | 1 Day before CTC | | |
|---|---|---|---|---|---|---|
| | Breakfast | Lunch | Dinner | Breakfast | Lunch | Dinner |
| Group 1 | | | | 250 cc 2.1% | 250 cc 2.1% | 250 cc 2.1% |
| Group 2 | | | | 250 cc 4% | 250 cc 2.1% | 250 cc 2.1% |
| Group 3 | 50 cc 4% | 50 cc 4% | 50 cc 4% | 250 cc 2.1% | 250 cc 2.1% | 250 cc 2.1% |
| Group 4 | | | | 25 cc 40% | 12.5 cc 40% | 12.5 cc 40% |
| Group 5 | 12.5 cc 40% | 12.5 cc 40% | 12.5 cc 40% | 25 cc 40% | 12.5 cc 40% | 12.5 cc 40% |

TABLE 2

Residual Stool: segmental distribution on a per-size basis.

| Patients | Cecum | Ascending Colon | Transverse Colon | Descending Colon | Sigmoid Colon | Rectum |
|---|---|---|---|---|---|---|
| 1 | 3 | 2-3 | 1-2-3 | 3 | 1 | 0 |
| 2 | 1-2-3 | 1-2-3 | 1 | 0 | 1 | 1-3 |
| 3 | 0 | 2-3 | 1-2 | 3 | 3 | 0 |
| 4 | 1-2 | 1-3 | 1-3 | 1 | 1-3 | 1 |
| 5 | 0 | 0 | 0 | 0 | 0 | 0 |
| 6 | 0 | 1 | 1-2 | 1-2 | 0 | 3 |
| 7 | 3 | 3 | 1 | 2-3 | 0 | 3 |
| 8 | 1-3 | 1-2-3 | 1 | 2-3 | 1-3 | 2-3 |
| 9 | 1-2-3 | 2-3 | 3 | 1-3 | 1-2-3 | 3 |
| 10 | 1, 2, 3 | 1, 2 | 0 | 0 | 1 | 1, 2 |
| 11 | 1, 2 | 1, 2, 3 | 1, 2, 3 | 1 | 1, 2, 3 | 3 |
| 12 | 1, 3 | 3 | 1, 2, 3 | 3 | 0 | 2, 3 |
| 13 | 1, 2 | 1, 2 | 1, 2 | 1, 2 | 0 | 3 |
| 14 | 3 | 0 | 0 | 0 | 0 | 1 |
| 15 | 1, 2, 3 | 1, 2 | 1 | 0 | 1, 2 | 3 |

0 = no residual stool;
1 = stool ≦5 mm;
2 = stool 6-9 mm;
3 = stool ≧1 cm.
Patients 1-3: group 1;
patients 4-6: group 2;
patients 7-9: group 3

TABLE 3

Residual Stool: segmental distribution based on the quantity

| Patients | Cecum | Ascending Colon | Transverse Colon | Descending Colon | Sigmoid Colon | Rectum |
|---|---|---|---|---|---|---|
| 1 | C | C | C | C | B | A |
| 2 | C | C | C | A | B | C |
| 3 | A | C | C | B | C | A |
| 4 | C | C | C | C | B | B |
| 5 | A | A | A | A | A | A |
| 6 | A | B | C | C | A | C |
| 7 | C | B | B | B | A | B |
| 8 | B | C | C | B | C | C |
| 9 | C | C | C | C | C | C |
| 10 | C | C | A | A | A | C |
| 11 | C | C | C | C | C | B |
| 12 | B | B | C | C | C | B |
| 13 | C | C | C | C | C | B |
| 14 | B | A | A | A | A | A |
| 15 | C | C | B | A | C | B |

A = No residual stool;
B = 1-10;
C > 10.
Patients 1-3: group 1;
patients 4-6: group 2;
patients 7-9: group 3.

TABLE 4

Segmental distribution of the fluid levels.

| Patients | Cecum | Ascending Colon | Transverse Colon | Descending Colon | Sigmoid Colon | Rectum |
|---|---|---|---|---|---|---|
| 1 | 1 | 1 | 1 | 1 | 1 | 1 |
| 2 | 1 | 1 | 1 | 1 | 1 | 1 |
| 3 | 1 | 1 | 1 | 1 | 1 | 1 |
| 4 | 2 | 1 | 1 | 1 | 1 | 1 |
| 5 | 2 | 1 | 1 | 1 | 1 | 1 |
| 6 | 1 | 1 | 1 | 1 | 1 | 1 |
| 7 | 1 | 1 | 1 | 1 | 1 | 1 |

TABLE 4-continued

Segmental distribution of the fluid levels.

| Patients | Cecum | Ascending Colon | Transverse Colon | Descending Colon | Sigmoid Colon | Rectum |
|---|---|---|---|---|---|---|
| 8 | 2 | 1 | 1 | 1 | 1 | 1 |
| 9 | 1 | 1 | 1 | 1 | 1 | 1 |
| 10 | 1 | 1 | 1 | 1 | 1 | 1 |
| 11 | 2 | 2 | 1 | 1 | 1 | 1 |
| 12 | 2 | 1 | 1 | 1 | 1 | 1 |
| 13 | 1 | 1 | 1 | 1 | 1 | 1 |
| 14 | 2 | 1 | 1 | 1 | 1 | 4 |
| 15 | 1 | 1 | 1 | 1 | 1 | 1 |

1 = 0%;
2 = <25% = less than 25% of the colonic lumen covered with fluid on at least 1 axial slice;
3 = 25-50% of the lumen;
4 = >50% of the lumen.
Patients 1-3: group 1;
patients 4-6: group 2;
patients 7-9: group 3.

TABLE 5

Segmental distribution of the barium layer, with appreciation of the thickness.

| Patients | Cecum | Ascending Colon | Transverse Colon | Descending Colon | Sigmoid Colon | Rectum |
|---|---|---|---|---|---|---|
| 1 | 0 | 1 | 0 | 0 | 0 | 0 |
| 2 | 1 | 0 | 0 | 0 | 0 | 0 |
| 3 | 1, 2 | 0 | 1 | 1, 2 | 0 | 0 |
| 4 | 1 | 1 | 1 | 0 | 0 | 0 |
| 5 | 1, 2 | 2 | 2, 3 | 2 | 0 | 2-3 |
| 6 | 1 | 0 | 0 | 0 | 1 | 0 |
| 7 | 1, 2, 3 | 1, 2 | 2 | 0 | 0 | 0 |
| 8 | 0 | 0 | 0 | 0 | 0 | 0 |
| 9 | 0 | 0 | 0 | 0 | 0 | 0 |
| 10 | 2 | 0 | 0 | 0 | 0 | 0 |
| 11 | 0 | 0 | 1 | 1 | 0 | 0 |
| 12 | 0 | 0 | 0 | 0 | 0 | 0 |
| 13 | 2 | 0 | 0 | 0 | 2 | 0 |
| 14 | 2, 3 | 2, 3 | 2, 3 | 2, 3 | 0 | 0 |
| 15 | 1 | 0 | 0 | 0 | 0 | 0 |

0 = No barium layer;
1 = thickness ≦5 mm;
2 = thickness 6-9 mm; thickness ≧1 cm.
Patients 1-3: group 1;
patients 4-6: group 2;
patients 7-9: group 3.

TABLE 6

Segments presenting without residue, with only residual stool ≦5 mm, with only a barium film ≦5 mm.

| Patients | Cecum | Ascending Colon | Transverse Colon | Descending Colon | Sigmoid Colon | Rectum |
|---|---|---|---|---|---|---|
| 1 | — | — | — | — | 2 | 1 |
| 2 | — | — | 2 | 1 | 2 | — |
| 3 | — | — | — | — | — | 1 |
| 4 | — | — | — | 2 | — | 2 |
| 5 | — | — | — | — | 1 | — |
| 6 | 3 | 2 | — | — | 3 | — |
| 7 | — | — | — | — | 2 | — |
| 8 | — | — | 2 | — | — | — |
| 9 | — | — | — | — | — | — |
| 10 | — | — | 1 | 1 | 2 | — |
| 11 | — | — | — | 2, 3 | — | — |

TABLE 6-continued

Segments presenting without residue, with only residual stool ≦5 mm, with only a barium film ≦5 mm.

| Patients | Cecum | Ascending Colon | Transverse Colon | Descending Colon | Sigmoid Colon | Rectum |
|---|---|---|---|---|---|---|
| 12 | — | — | — | — | — | — |
| 13 | — | — | — | — | — | — |
| 14 | — | — | — | — | 1 | — |
| 15 | — | — | 2 | 1 | 1 | — |

—: not applicable.
1: empty segments.
2: segments with residual stool ≦5 mm.
3: segmenst with a barium layer ≦5 mm.

TABLE 8

Table showing the densities of the tagged stool

| | Cecum | Ascend | Transv | Descend | Sigm | Rectum |
|---|---|---|---|---|---|---|
| 1 | 895 | 955 | 877 | 890 | 812 | 816 |
| 2 | 843 | 1015 | 919 | 591 | 932 | 545 |
| 3 | 1094 | 988 | 854 | 861 | 805 | 943 |
| 4 | 1541 | 1526 | 1466 | 1353 | 1468 | 1064 |
| 5 | 1040 | 1007 | 1022 | 1172 | 1267 | 984 |

The trials described above show that by combining a low residue diet and a hydration control the day before CT colonography, efficacious tagging of fecal residue in the colon was obtained using barium as the sole fecal tagging agent administered at a volume of as less as 50 ml administered over 1 day. Such results were obtained with subject to individuals to a cathartic cleansing before the predetermined activity. Both the reduction of the barium volume and the short time span of barium administration (1 day) will increase patient compliance. Together with the omission of the cathartic cleansing, this could dramatically improve the patient attendance to a screening program for colorectal cancer.

While the above embodiments and descriptions are disclosed in details they are not meant to limit the scope of the claimed invention. Indeed, it will be appreciated by those skilled in the art that various changes and modifications to the subject invention can be made without departing from the spirit and scope of the invention. For example, one skilled in the area would recognize that the present invention encompasses variations of the embodiments discussed herein. Therefore, different food products may be substituted for the specific food products described herein and the layout of the kit may be modified. Also, food items may be substituted among and between each other. Also, the invention may suitably comprise, consist of or consist essentially of the elements described herein. Further, the invention described herein suitably may be practiced in the absence of any element which is not specifically disclosed herein.

We claim:

1. A method of preparing an individual for a predetermined activity, wherein said predetermined activity requires the tagging of at least some colonic residue in the individual's digestive tract, said method comprising:
   (a) administering 3 doses of a tagging agent in an aqueous suspension over a 20 to 36 hour administration period; wherein each dose of tagging agent is a volume of about 20 ml and comprises about 40% w/v tagging agent; and
   (b) administering about 1 to 4 liters of total fluid over the 20 to 36 hour administration period with the patient free from administration of laxatives or cathartics for at least 24 hours.

2. The method of claim 1, wherein the total fluid intake is 1 to 3 liters over the 20 to 36 hour administration period.

3. The method of claim 1, wherein the tagging agent is Barium Sulfate.

4. The method of claim 1, wherein the tagging agent is combined with Sorbitol or Mannitol.

5. A method for generating radiography images of one or more sections of an individual's gastrointestinal tract for screening, comprising
   (i) administering to the individual a low residue diet over at least a 48-hour period;
   (ii) administering to the individual 3 doses of a tagging agent over the at least 48-hour period, the tagging agent being an aqueous suspension at a volume of about 20 mL and comprising about 40% w/v tagging agent;
   (iii) with the patient free from administration of laxatives or cathartics for at least 24 hours, imaging the one or more sections of the individual's gastrointestinal tract after the administration period;
   (iv) producing a radiography image of the one or more sections of the individual's gastrointestinal tract; said image showing stool marked with the tagging agent; and
   (v) screening the radiography image to identify the presence of any abnormality in the gastrointestinal tract without removing and/or subtracting the marked stool from the images.

6. The method of claim 5, wherein the images are produced in connection with a predetermined activity, including sigmoidscopy, fiberoptic colonscopy, CT colonography or MR colonography of the individual's colon.

7. The method of claim 5, wherein the total fluid intake is 1 to 3 liters over a 20 to 36 hour administration period.

8. The method of claim 5, wherein the tagging agent is Barium Sulfate.

* * * * *